US010209262B2

(12) United States Patent
Hayasaki

(10) Patent No.: US 10,209,262 B2
(45) Date of Patent: Feb. 19, 2019

(54) BLOOD SAMPLE ANALYZING METHOD, BLOOD SAMPLE ANALYZER, AND SYSTEM

(71) Applicant: SYSMEX CORPORATION, Kobe-shi, Hyogo (JP)

(72) Inventor: Junki Hayasaki, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 208 days.

(21) Appl. No.: 15/242,694

(22) Filed: Aug. 22, 2016

(65) Prior Publication Data

US 2017/0059593 A1    Mar. 2, 2017

(30) Foreign Application Priority Data

Aug. 28, 2015 (JP) ................................. 2015-169547

(51) Int. Cl.
| | |
|---|---|
| G01N 33/86 | (2006.01) |
| G01N 33/483 | (2006.01) |
| G01N 33/49 | (2006.01) |
| G01N 21/82 | (2006.01) |

(Continued)

(52) U.S. Cl.
CPC .......... *G01N 33/86* (2013.01); *G01N 21/272* (2013.01); *G01N 21/82* (2013.01); *G01N 21/75* (2013.01); *G01N 33/483* (2013.01); *G01N 33/49* (2013.01); *G01N 2333/075* (2013.01); *G01N 2333/75* (2013.01); *G01N 2800/224* (2013.01)

(58) Field of Classification Search
CPC ...... G01N 21/272; G01N 21/75; G01N 21/82; G01N 2333/075; G01N 2333/75; G01N 2800/224; G01N 33/49; G01N 33/86; G01N 33/483

USPC ...... 436/63, 69, 164; 435/13, 288.7; 422/73, 422/82.05, 82.09; 600/369; 73/64.41, 73/64.43

See application file for complete search history.

(56) References Cited

U.S. PATENT DOCUMENTS

| 6,524,861 B1 | 2/2003 | Anderson |
| 9,910,052 B2 * | 3/2018 | Ishikura ................. G01N 33/86 |

(Continued)

FOREIGN PATENT DOCUMENTS

| EP | 2 413 144 A2 | 2/2012 |
| EP | 2 413 144 A3 | 2/2012 |
| EP | 2 775 292 A1 | 9/2014 |

OTHER PUBLICATIONS

Hidesaku Asakura et al., "Application and Usage of Hemostatic Drug and Antifibrinolytic Drug", Thrombosis and Hemostasis Magazine, 2009, pp. 285-288, vol. 20, No. 3.

*Primary Examiner* — Maureen Wallenhorst
(74) *Attorney, Agent, or Firm* — Sughrue Mion, PLLC

(57) ABSTRACT

Disclosed is a blood sample analyzing method including preparing a measurement specimen by mixing a blood sample with a measuring reagent of fibrin and a fibrinogen degradation product (FDP); acquiring, based on a time-dependent change in optical information obtained by optically measuring the measurement specimen, first information indicating an FDP concentration and second information indicating a curving degree of a time course curve showing the time-dependent change of the optical information; and determining an enhanced fibrinolytic state of the blood sample or acquiring a value related to a D dimer of the blood sample based on the first information and the second information.

20 Claims, 25 Drawing Sheets

(51) Int. Cl.
  *G01N 21/75* (2006.01)
  *G01N 21/27* (2006.01)

(56) References Cited

U.S. PATENT DOCUMENTS

| | | | |
|---|---|---|---|
| 2009/0004673 A1* | 1/2009 | Ono | C12Q 1/37 435/7.1 |
| 2009/0305301 A1* | 12/2009 | Mirshahi | C12Q 1/56 435/7.1 |
| 2011/0014640 A1* | 1/2011 | Yamamoto | G01N 21/5907 435/13 |
| 2012/0028370 A1 | 2/2012 | Nagai et al. | |
| 2013/0143243 A1 | 6/2013 | Kobayashi et al. | |
| 2017/0363651 A1* | 12/2017 | Hayasaki | G01N 21/49 |

* cited by examiner

FIG. 25

MEASUREMENT RESULT DISPLAY SCREEN — 100

| DATE AND TIME | SAMPLE NUMBER | FDP MEASURED VALUE | ENHANCED FIBRINOLYTIC FLAG 101 | FDP/DD ESTIMATED VALUE 102 | DD ESTIMATED VALUE 103 |
|---|---|---|---|---|---|
| 15/5/6 | 00001 | 53 μg/mL | ENHANCED FIBRINOLYSIS | 2.0 | 26 μg/mL |
| 15/5/6 | 00002 | 108 μg/mL | ENHANCED FIBRINOLYSIS | 3.0 | 36 μg/mL |
| 15/5/6 | 00003 | 34 μg/mL |  | 2.0 | 17 μg/mL |
| 15/5/6 | 00004 | 15 μg/mL |  | 1.5 | 10 μg/mL |
| ..... | ..... | ..... | ..... | ..... | ..... |

RESULT OF OTHER ITEMS

BLOOD SAMPLE ANALYZING METHOD, BLOOD SAMPLE ANALYZER, AND SYSTEM

CROSS REFERENCE TO RELATED APPLICATIONS

This application claims priority from prior Japanese Patent Application No. 2015-169547, filed on Aug. 28, 2015, entitled "BLOOD SAMPLE ANALYZING METHOD, BLOOD SAMPLE ANALYZER, AND COMPUTER PROGRAM", the entire contents of which are incorporated herein by reference.

TECHNICAL FIELD

The present invention relates to a blood sample analyzing method, a blood sample analyzer, and a system.

BACKGROUND

In addition to the disseminated intravascular coagulation (DIC) in which coagulation activity is dominant, enhanced fibrinolytic type DIC is known as the DIC. In particular, in the DIC associated with acute promyelocytic leukemia (APL), it is assumed that enhanced fibrinolytic type DIC occurs. In the enhanced fibrinolytic type DIC, the lytic action is enhanced to an extent greater than the extent of thrombus formation, thus presenting bleeding symptoms. However, the conventional DIC treatment is an anticoagulation treatment of administering heparin for thrombolysis, and such treatment may not be suitable for the enhanced fibrinolytic type DIC. As symptoms differ depending on the underlying disease, it is important to classify the DIC into to the DIC in which the coagulation activity is dominant and the enhanced fibrinolytic type DIC, and determine the treatment policy.

For example, "3. Antifibrolytic agent (adaptation and usage of hemostatic and antifibrolytic agent)," The Journal of Japanese Society on Thrombosis and Hemostasis Vol. 20 (2009), by Hidesaku ASAKURA et al., The Japanese Society on Thrombosis and Hemostasis discloses use of a fibrin and fibrinogen degradation product (FDP) concentration and an FDP/D dimer ratio for the determination of the enhanced fibrinolytic type DIC. More specifically, "3. Antifibrolytic agent (adaptation and usage of hemostatic and antifibrolytic agent)," The Journal of Japanese Society on Thrombosis and Hemostasis Vol. 20 (2009), by Hidesaku ASAKURA et al., The Japanese Society on Thrombosis and Hemostasis discloses the following conditions for examination finding in the guideline for carrying out the diagnosis of disease conditions of the enhanced fibrinolytic type DIC. Hereinafter, DD refers to a D dimer. Examination findings: Two or more of the following are satisfied.
1) FDP ≥80 µg/ml
2) fibrinogen <100 mg/dl
3) High value of FDP/DD ratio (low value of DD/FDP ratio)

If the diagnosis of disease conditions of the enhanced fibrinolytic type DIC includes determination on whether or not at least 3) above is satisfied, the FDP measurement and the D dimer measurement are required to obtain the FDP/DD ratio.

As shown in U.S. Patent Application Serial No. 2013/0143243 and US Patent Application Serial No. 2012/0028370, the FDP measurement is carried out using an FDP measuring reagent, and the D dimer measurement is carried out using a D dimer measuring reagent. Thus, different reagents are used for the FDP measurement and the D dimer measurement, so that the measurements are separately carried out.

The FDP measurement and the D dimer measurement are required, as described above, in the diagnosis guideline of the enhanced fibrinolytic type DIC described in "3. Antifibrolytic agent (adaptation and usage of hemostatic and antifibrolytic agent)," The Journal of Japanese Society on Thrombosis and Hemostasis Vol. 20 (2009), by Hidesaku ASAKURA et al., The Japanese Society on Thrombosis and Hemostasis. Thus, at least two measurements are required, which is cumbersome and leads to increase in cost.

Some examination facilities carry out the FDP measurement and the D dimer measurement not simultaneously, or carry out only the FDP measurement and not the D dimer measurement. In this case, it may be cumbersome to carry out the sample analysis that requires the D dimer measurement as in the determination of the enhanced fibrinolytic type DIC.

SUMMARY OF THE INVENTION

The scope of the present invention is defined solely by the appended claims, and is not affected to any degree by the statements within this summary.

A first aspect of the present invention relates to a blood sample analyzing method including preparing a measurement specimen by mixing a blood sample with a measuring reagent of fibrin and a fibrinogen degradation product (FDP); acquiring, based on a time-dependent change in optical information obtained by optically measuring the measurement specimen, first information indicating an FDP concentration and second information indicating a curving degree of a time course curve showing the time-dependent change of the optical information; and determining an enhanced fibrinolytic state of the blood sample based on the first information and the second information.

A second aspect of the present invention relates to a blood sample analyzer including a specimen preparing unit that prepares a measurement specimen by mixing a blood sample with a measuring reagent of fibrin and a fibrinogen degradation product (FDP); a detection unit that optically measures the measurement specimen and outputs a detection signal; an acquiring unit that acquires optical information of the measurement specimen obtained from the detection signal; and a processing unit that acquires first information indicating an FDP concentration and second information indicating a curving degree of a time course curve showing a time-dependent change of the optical information based on the optical information, and determines an enhanced fibrinolytic state of the blood sample based on the first information and the second information.

A third aspect of the present invention relates to a computer program for causing a computer to execute a sample analyzing process, the sample analyzing process including a first process of acquiring, based on a time-dependent change of optical information obtained by optically measuring a measurement specimen that is a mixture of a measuring reagent of fibrin and a fibrinogen degradation product (FDP) and a blood sample, first information indicating an FDP concentration and second information indicating a curving degree of a time course curve showing the time-dependent change of the optical information; and a second process of determining an enhanced fibrinolytic state of the blood sample based on the first information and the second information.

A fourth aspect of the present invention relates to a blood sample analyzing method including preparing a measurement specimen by mixing a blood sample with a measuring reagent of fibrin and a fibrinogen degradation product (FDP); acquiring, based on a time-dependent change in optical information obtained by optically measuring the measurement specimen, first information indicating an FDP concentration and second information indicating a curving degree of a time course curve showing the time-dependent change of the optical information; and acquiring a value related to a D dimer of the blood sample based on the first information and the second information.

A fifth aspect of the present invention relates to a blood sample analyzer including a specimen preparing unit that prepares a measurement specimen by mixing a blood sample with a measuring reagent of fibrin and a fibrinogen degradation product (FDP); a detection unit that optically measures the measurement specimen and outputs a detection signal; an acquiring unit that acquires optical information of the measurement specimen obtained from the detection signal; and a processing unit that acquires first information indicating an FDP concentration and second information indicating a curving degree of a time course curve showing a time-dependent change of the optical information based on the optical information, and acquires a value related to a D dimer of the blood sample based on the first information and the second information.

A sixth aspect of the present invention relates to a computer program for causing a computer to execute a sample analyzing process, the sample analyzing process including a first process of acquiring, based on a time-dependent change of optical information obtained by optically measuring a measurement specimen that is a mixture of a measuring reagent of fibrin and a fibrinogen degradation product (FDP) and a blood sample, first information indicating an FDP concentration and second information indicating a curving degree of a time course curve showing the time-dependent change of the optical information; and a second process of acquiring a value related to a D dimer of the blood sample based on the first information and the second information.

A seventh aspect of the present invention relates to a system adapted to a method for executing a sample analyzing process, including: a processor, and a memory, under control of the processor, including software instructions adapted to enable the system to execute the sample analyzing process including: a first process of acquiring, based on a time-dependent change of optical information obtained by optically measuring a measurement specimen that is a mixture of a measuring reagent of fibrin and a fibrinogen degradation product (FDP) and a blood sample, first information indicating an FDP concentration and second information indicating a curving degree of a time course curve showing the time-dependent change of the optical information; and a second process of determining an enhanced fibrinolytic state of the blood sample based on the first information and the second information.

BRIEF DESCRIPTION OF THE DRAWINGS

FIG. 25 is a diagram showing a result display screen.

DETAILED DESCRIPTION OF THE PREFERRED EMBODIMENT

1. Outline of Sample Analyzing Method and Sample Analyzer

Figure 1:
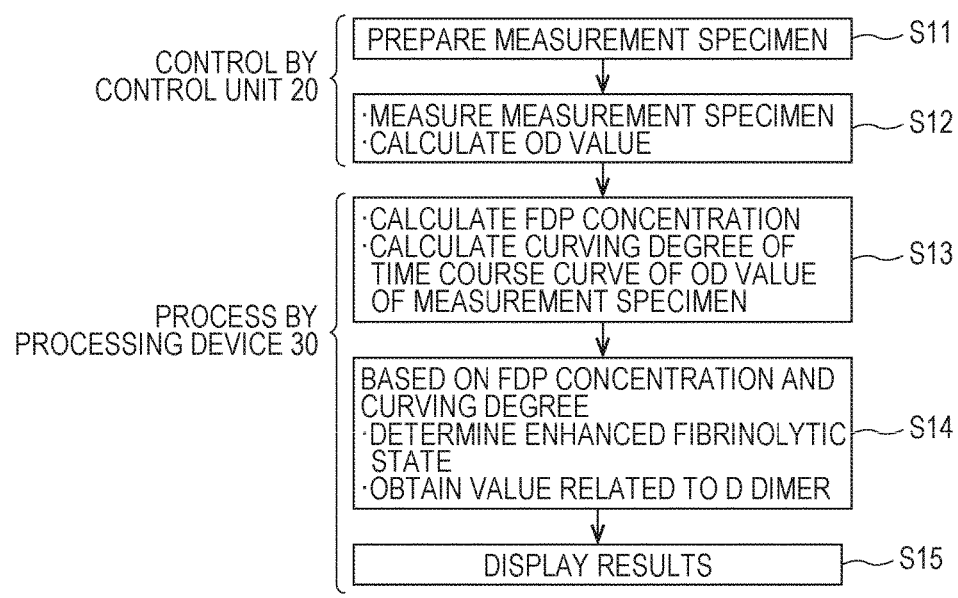
FIG. 1 is a flowchart showing a procedure of a sample analyzing process.
Figure 2:
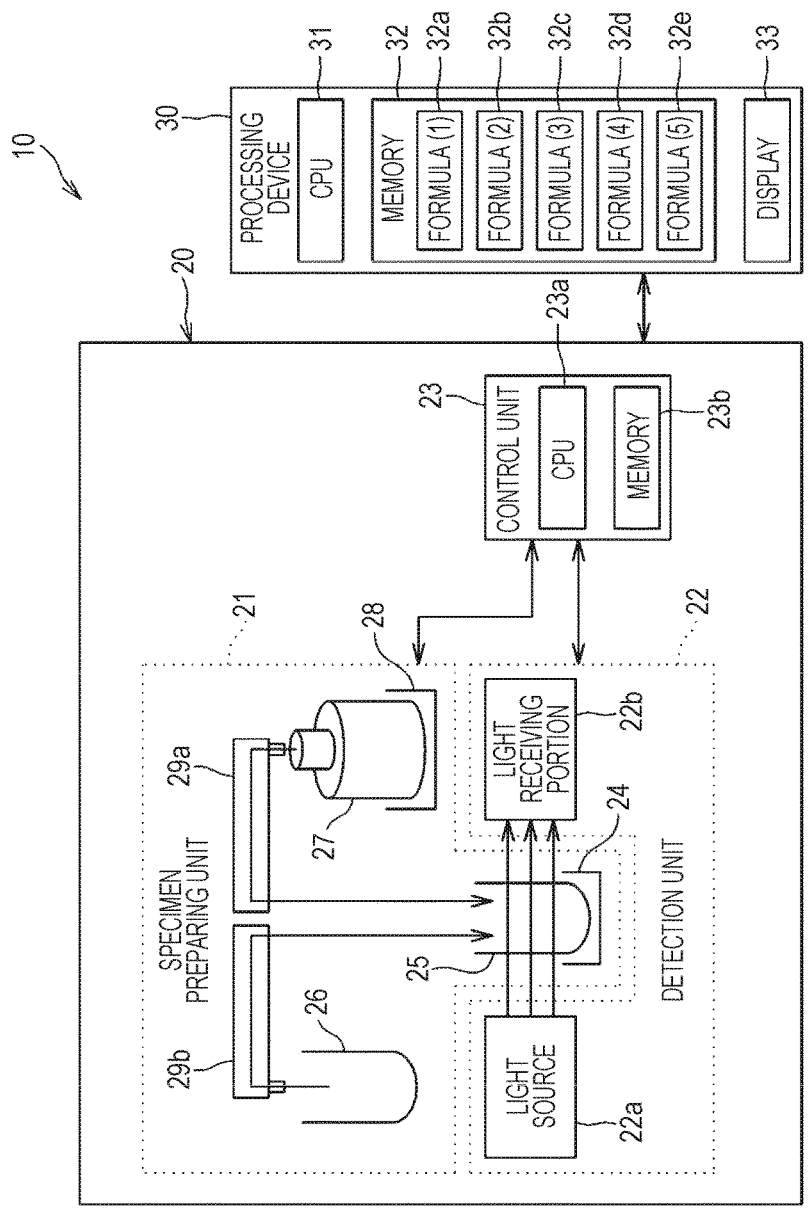
FIG. 2 is a configuration diagram of a blood sample analyzer.

The sample analyzing method according to an embodiment includes step S11 to step S15 shown in FIG. 1. Step S11 to step S15 are executed by a blood sample analyzer 10 shown in FIG. 2. The blood sample analyzer 10 measures a blood sample collected from a subject through, for example, an immunoturbidimetric method to analyze the blood sample. The blood sample to be analyzed is, for example, blood plasma. The blood sample may be blood serum or whole blood.

The blood sample analyzer 10 includes a measuring device 20 and a processing device 30. The measuring device 20 measures a measurement specimen containing the blood sample. The processing device 30 analyzes the measurement result acquired from the measuring device 20.

The measuring device 20 includes a specimen preparing unit 21, a detection unit 22, and a control unit 23. The specimen preparing unit 21 includes a cuvette holding portion 24, a reagent setting portion 28, a reagent dispensing portion 29a, and a sample dispensing portion 29b. The cuvette holding portion 24 holds a cuvette 25. The cuvette 25 is a container for preparing the measurement specimen. A reagent container 27 containing a reagent is set in the reagent setting portion 28. The reagent dispensing portion 29a aspirates the reagent from the reagent container 27 set in the reagent setting portion 28, and dispenses the reagent into the cuvette 25. The sample dispensing portion 29b aspirates the blood sample from the sample container 26, and dispenses the blood sample into the cuvette 25. The sample container 26 is transported to a sample aspirating position by the sample dispensing portion 29b by a transportation device (not shown).

The reagent contained in the reagent container 27 includes a reagent for the FDP measurement. Various types of commercially available FDP measuring reagents can be used for the FDP measuring reagent, and for example, FDP measurement kit LIAS AUTO P-FDP reagent manufactured by Sysmex Corporation, LPIA FDP-P reagent manufactured by LSI Medience Corporation, and the like can be used.

In step S11 of FIG. 1, the specimen preparing unit 21 mixes the blood sample dispensed into the cuvette 25 with the reagent dispensed into the cuvette 25, and prepares a measurement specimen for the FDP measurement (hereinafter, a "measurement specimen" refers to a "measurement specimen for FDP measurement"). The operation for preparing the specimen by the specimen preparing unit 21 is controlled by the control unit 23.

The detection unit 22 includes a light source 22a and a light receiving portion 22b. The light source 22a is disposed to irradiate the measurement specimen in the cuvette 25 with light. The light source 22a includes, for example, a halogen lamp or an LED. The wavelength of the light emitted from the light source 22a has only to be a wavelength suited for the measurement, and is, for example, 800 nm, 575 nm, or 730 nm.

The light receiving portion 22b receives transmitted light or scattered light from the measurement specimen, and outputs a detection signal, which is an electric signal corresponding to the received light amount, as a measurement result. The light receiving portion 22b includes, for example, a photodiode.

In step S12 of FIG. 1, the detection unit 22 measures the turbidity of the measurement specimen, and outputs a detection signal indicating the time-dependent change in the turbidity of the measurement specimen. The detection signal may be a signal indicating the time-dependent change of the transmitted light or the scattered light that has passed through the measurement specimen. For example, when measuring the turbidity of the measurement specimen by the immunoturbidimetric method, the light receiving portion 22b receives the light emitted from the light source 22a and passed through the measurement specimen. As the agglutination reaction of the immune complex advances in the measurement specimen, the turbidity of the measurement specimen rises, and hence the light amount of the transmitted light reduces, and the output level of the electric signal lowers with elapse of time. Therefore, the detection signal output from the light receiving portion 22b indicates the time-dependent change in the turbidity of the measurement specimen.

The control unit 23 receives the detection signal from the detection unit 22, and calculates optical information based on the detection signal. The control unit 23 functions as an acquiring unit that acquires the optical information. The optical information is, for example, an optical density (OD) value. The OD value is calculated based on an increase rate of the turbidity indicated by the detection signal. The OD value may be calculated not from the turbidity but, for example, from the transmitted light intensity. The control unit 23 calculates time series data of the OD value for a period from the start of measurement until the end of measurement based on the detection signal of the period from the start of measurement until the end of measurement. The time series data of the OD value is data indicating the time-dependent change in the OD value, that is, the change in the OD value that appears following the elapse of time, and indicates a time course curve of the optical information of the measurement specimen. The control unit 23 transmits the time series data of the calculated OD value to the processing device 30.

The control unit 23 includes a CPU 23a and a memory (storage unit) 23b. The control unit 23 executes the computer program stored in the memory 23b by the CPU 23a to fulfill the function of the control unit 23.

The processing device 30 includes a CPU 31, a memory (storage unit) 32, and a display 33. The processing device 30 executes the computer program stored in the memory 32 by the CPU 31 to fulfill the function of the processing device 30.

The processing device 30 receives the time series data of the OD value from the control unit 23. In step S13 of FIG. 1, the processing device 30 calculates first information and second information from the time series data of the OD value. The first information is information indicating the FDP concentration. The second information is information indicating a curving degree of the time course curve of the OD value of the measurement specimen.

In step S14, the processing device 30 determines the enhanced fibrinolytic state of the blood sample based on the first information indicating the FDP concentration and the second information indicating the curving degree. The processing device 30 obtains a value related to the D dimer based on the first information indicating the FDP concentration and the second information indicating the curving degree. The value related to the D dimer is, for example, an estimated value of the D dimer concentration or a value calculated from the D dimer concentration. The value calculated from the D dimer concentration is, for example, the FDP/D dimer ratio.

The memory 32 of the processing device 30 includes analysis information 32a, 32b, 32c, 33d, and 34e to determine the enhanced fibrinolytic state and obtain the value related to the D dimer. The analysis information 32a, 32b, 32c, 33d, and 34e each correspond to formulae (1) to (5) to be described later. The CPU 31 of the processing device 30 uses the first information indicating the FDP concentration and the second information indicating the curving degree, as well as the analysis information stored in the memory 32 to determine the enhanced fibrinolytic state and obtain the value related to the D dimer. Each of formulae (1) to (5) will be described later.

In step S15, the processing device 30 displays a result display screen on the display 33. The result display screen can display the determination result of the enhanced fibrinolytic state, the value related to the D dimer, and other measurement results. The result display screen will also be described later.

2. Sample Analyzing Process by Processing Device

2.1 FDP Concentration

The processing device 30 calculates the first information indicating the FDP concentration from the time series data of the OD value indicating the time course curve of the OD value of the measurement specimen. The FDP concentration is calculated according to the FDP concentration calculation procedure described in the attached document of the FDP measuring reagent used for the FDP measurement. Specifically, the processing device 30 obtains the amount of change per predetermined time (e.g., one minute) of the OD value, which is the optical information, and applies the obtained amount of change to a standard curve obtained from a calibrator to calculate the FDP concentration in the measurement specimen.

The first information indicating the FDP concentration may be information directly indicating the FDP concentration, or may be information indirectly indicating the FDP concentration such as a parameter correlated with the FDP concentration. The information directly indicating the FDP concentration is, for example, the FDP concentration calculated according to the above-mentioned FDP concentration calculation procedure. The information indirectly indicating the FDP concentration is, for example, amount of change per predetermined time of the OD value. The amount of change per predetermined time of the OD value is correlated with the FDP concentration, as can be seen from the fact that it is also used in the calculation of the FDP concentration, and thus indirectly indicates the FDP concentration.

2.2 Calculation of Curving Degree of Time Course Curve and Enhanced Fibrinolysis According to the guideline described in "3. Antifibrolytic agent (adaptation and usage of hemostatic and antifibrolytic agent)," The Journal of Japanese Society on Thrombosis and Hemostasis Vol. 20 (2009), by Hidesaku ASAKURA et al., The Japanese Society on Thrombosis and Hemostasis, the FDP measurement and the D dimer measurement are required to determine the enhanced fibrinolytic state of the blood sample using the FDP/DD ratio. However, the inventor of the present invention surprisingly found that the determination of the enhanced fibrinolytic state, which required the D dimer measurement until now, can be carried out by the FDP measurement without carrying out the D dimer measurement.

More specifically, the inventor of the present invention found a correlation between the shape of the time course curve of the optical information of the measurement specimen and the enhanced fibrinolytic state. The correlation found by the inventor of the present invention is that the curving degree of the time course curve indicating the time-dependent change of the optical information of the measurement specimen is associated with the enhanced fibrinolytic state. Through the use of such correlation, the determination on the enhanced fibrinolytic state can be carried out based on the result of the FDP measurement.

The optical information of the measurement specimen is information obtained by optically measuring the measurement specimen, and is, for example, the optical concentration (OD) value. The time course curve of the optical information of the measurement specimen is a curve indicating the time-dependent change of the optical information of the measurement specimen prepared using the FDP measurement specimen, and is basically a curve C shown in FIG. 3. The time course curve is drawn based on the time series data of the OD value acquired by the processing device 30.

Figure 3:
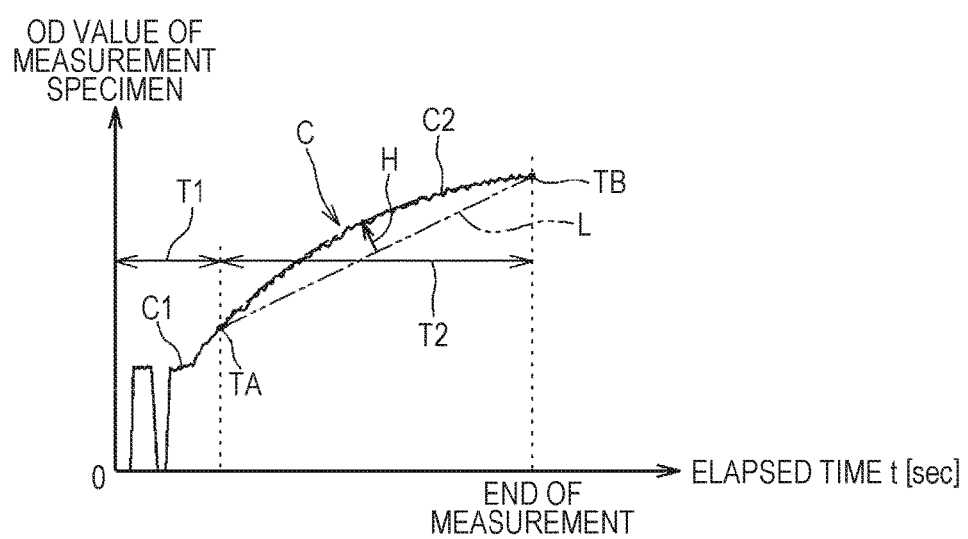
FIG. 3 is a graph showing a time course curve.

In FIG. 3, the horizontal axis indicates an elapsed time from the start of measurement of the measurement specimen, and the vertical axis indicates the OD value of the measurement specimen. The curving degree of the time course curve is the bending extent of the time course curve of the optical information that increases time dependently. The OD value increases while repeating small increase and decrease, but the fluctuation in the time course curve by such small increase and decrease is not taken into consideration. Instead, the curvature of the time course curve as seen macroscopically will be considered.

In many cases, the time course curve of the OD value of the measurement specimen includes a curve portion C1 of a first period T1 from the start of measurement (elapsed time=0 sec) to several tens of seconds, and a curve portion C2 of a second period T2 following the first period T1 to the end of measurement. The first period T1 is, for example, 30 seconds. The OD value monotonically increases in the second period T2, but the turbidity of the measurement specimen does not stabilize and a large increase and decrease of the OD value may occur in the first period T1. Such a first period T1 does not appropriately indicate the time-dependent change of the OD value, and thus the curving degree can be more accurately obtained with the first period T1 excluded when calculating the curving degree of the time course curve C. If the OD value monotonically increases stably in the first period T1 as well, the curve portion C1 in the first period T1 may be taken into consideration when calculating the curving degree of the time course curve C.

For example, considering the curving degree of the time course curve C in a range from a starting point TA to a terminating point TB of the second period T2 in the time course curve C of FIG. 3, the larger a projection amount H is toward the upper side of the time course curve C from a line L connecting the starting point TA with the terminating point TB, the more greatly the curve is bent and the larger the curving degree is. On the contrary, the smaller the projection amount H is, the smaller the curving degree is.

In many cases, as shown in FIG. 3, the time course curve of the OD value is a curve convex toward the upper side in the second period T2, where the projection amount H is a positive value. However, in the case of a blood sample collected from a subject in whom a factor forming the D dimer is deficit, the curve may be convex toward the lower side with respect to the line L, and in this case, the curving degree and the projection amount H are negative values.

The processing device 30 calculates the second information indicating the curving degree of the time course curve from the time series data of the OD value. The curving degree can be indicated by various indices.

2.3 Variation of Indices Indicating Curving Degree

Figure 4A:
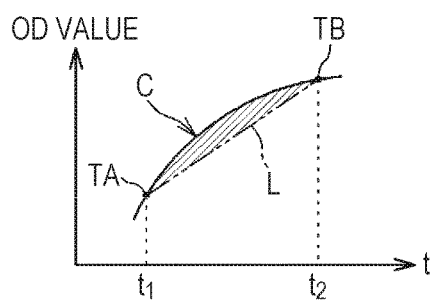
FIGS. 4A, 4B, 4C, 4D, 4E and 4F show a variation diagrams of indices indicating a curving degree of the time course curve.

FIGS. 4A to 4F show variations of the second information indicating the curving degree. A first example of the second information indicating the curving degree is an area of a convex area of the time course curve. As shown in FIG. 4A, the area of the convex area is calculated as a size of a region surrounded by the line L connecting the starting point TA with the terminating point TB of a target period for area calculation in the time course curve, and the time course curve C. The curving degree can be accurately obtained by setting the starting point TA to the terminating point TB of the target period of calculation within a period in which the OD value of the measurement specimen monotonically increases as in the second period T2 of FIG. 3. The area of an area above the line L is preferably regarded as a positive value, and the area of an area below the line L is preferably regarded as a negative value.

The greater the curving degree from the line L toward the upper side is, the more the area of the convex area increases, and the smaller the curving degree toward the upper side is, the more the area of the convex area decreases.

A second example of the second information indicating the curving degree is a curvature radius or a curvature of the time course curve C. The time course curve is curve approximated by, for example, a monotonically increasing curve, and the curvature radius or the curvature of the approximated curve is regarded as the curvature radius or the curvature of the time course curve. The time course curve can be viewed macroscopically ignoring the fluctuation in the time course curve caused by the small increase and decrease by curve approximating the time course curve C.

The curvature radius or the curvature of a case where the time course curve C is convex toward the upper side is preferably regarded as a positive value, and the curvature radius or the curvature of a case where the time course curve C is convex toward the lower side is preferably regarded as a negative value. If the curvature radius or the curvature changes from the starting point TA to the terminating point TB of the calculation target range of the curvature radius or the curvature, an average of the curvature radius or an average of the curvature of a plurality of points P1, P2, P3, and P4 within the target period may be obtained as the second information as shown in FIG. 4B.

A third example of the second information indicating the curving degree is a coefficient of a case where the time course curve C is polynomially approximated. For example, a coefficient a of a case where the time course curve is approximated by a quadratic function of ax2+bx+c can be regarded as the second information.

A fourth example of the second information indicating the curving degree is the projection amount H of the time course curve. As shown in FIG. 4C, the projection amount H is calculated as a length extending perpendicularly from a middle point P of the line L connecting the starting point TA with the terminating point TB of the calculation target range of the projection amount H toward the time course curve C, and reaching the time course curve C. The projection amount H of a case where the time course curve C is convex toward the upper side is preferably regarded as a positive value, and the projection amount H of a case where the time course curve C is convex toward the lower side is preferably regarded as a negative value.

Figure 4D:
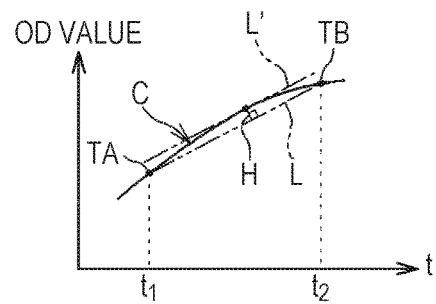
Figure 4B:
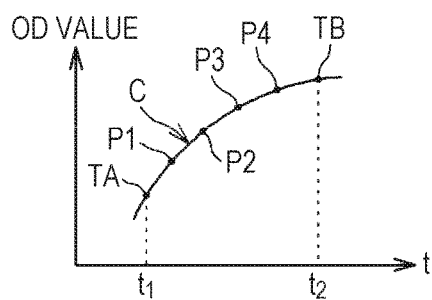

As shown in FIG. 4D, the projection amount H may be an interval between a line L' parallel to the line L and the straight line L, where the line L' is a tangent line of the time course curve C from the starting point TA to the terminating point TB of the calculation target range of the projection amount H.

Figure 4E:
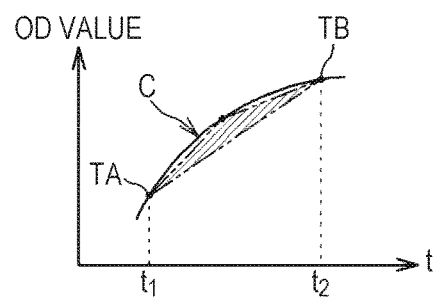
Figure 4C:
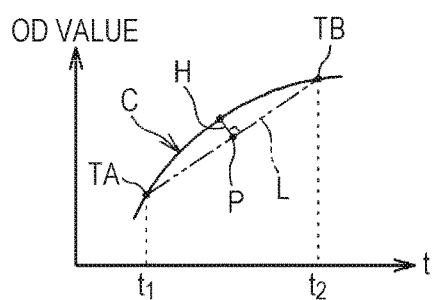

A fifth example of the second information indicating the curving degree is an area of an approximated figure of the convex area. The area of the approximated figure of the convex area is one of the variations of the information indicating the size of the area of the convex area in the first example. As shown in FIG. 4E, the approximated figure of the convex area may be, for example, a triangle approximating a region surrounded by the line L connecting the starting point TA with the terminating point TB of the target range for calculation of the area, and the time course curve C. The approximated figure may be a semi-circle or an arbitrary polygon.

Figure 4F:
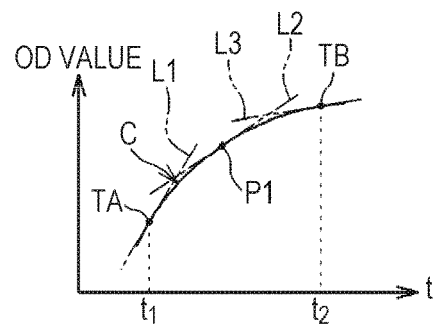

A sixth example of the second information indicating the curving degree is a ratio between two arbitrary slopes of the slopes of tangent lines L1, L2, and L3 or regression lines of the time course curve C. As shown in FIG. 4F, the slope of the tangent line or the regression line is, for example, calculated as a slope of the tangent line L1 or the regression line at the beginning (e.g., starting point TA or vicinity thereof) of the time course curve, a slope of the tangent line L2 or the regression line at the middle (e.g., point P1 between starting point TA and terminating point TB) of the time course curve, or a slope of the tangent line L3 or the regression line at the end (e.g., terminating point TB or vicinity thereof) of the time course curve. The ratio between the slopes of the two arbitrary slopes of the tangent lines L1, L2, and L3, or the regression lines calculated in such a manner can be calculated as the second information. The second information is, for example, slope of L1/slope of L2, slope of L2/slope of L1, or slope of L3/slope of L1. The plurality of tangent lines or regression lines may be divided into two groups, the sum or the average of the slopes may be calculated in each group, and the ratio of the sum or the average of the slope between the two groups may be calculated as the second information. For example, in the first half of the time course curve, the slopes of each of the three tangent lines may be calculated, and a first average value thereof may be calculated. Similarly, in the second half of the time course curve as well, the slopes of each of the three tangent lines may be calculated, and a second average value thereof may be calculated. The ratio between the first average value and the second average value can be calculated as the second information.

2.4 Calculation Example of Area of Convex Area

Hereinafter, the area of the convex area of the first example will be adopted for the second information indicating the curving degree. The processing device 30 calculates the area of the convex area using the following formula (1) from the time series data of the OD value. Formula (1) is stored in the memory 32 as the analysis information 32a.

[Formula 1]

$$\text{Area of convex area} = \sum_{t=30}^{150} \frac{(OD(t)) - a \times t - b}{1000} \quad (1)$$

In the formula, t is a time [sec] in the time course curve, OD(t) is the OD value at time t (second), and a×t−b is a regression expression of a line connecting the starting point TA for the curving degree calculation with the terminating point TB for the curving degree calculation in the time course curve. The starting point TA here is the OD value at the time point of 30 seconds from the start of measurement (t=0), and the terminating point TB is the OD value at the time point of 150 seconds from the start of measurement. The starting point TA may be an average value of the FDP concentration during a period (e.g., 27.5 to 32.5 seconds) near the starting point reference (e.g., 30 seconds), and the terminating point TB may be an average value of the FDP concentration during a period (e.g., 147.5 to 152.5 seconds) near the terminating point reference (e.g., 150 seconds). In the case of the dilution measurement, a value obtained by multiplying a dilution factor by the area of the convex area calculated using formula (1) can be regarded as the area of the convex area.

2.5 Determination of Enhanced Fibrinolytic State

Figure 5:
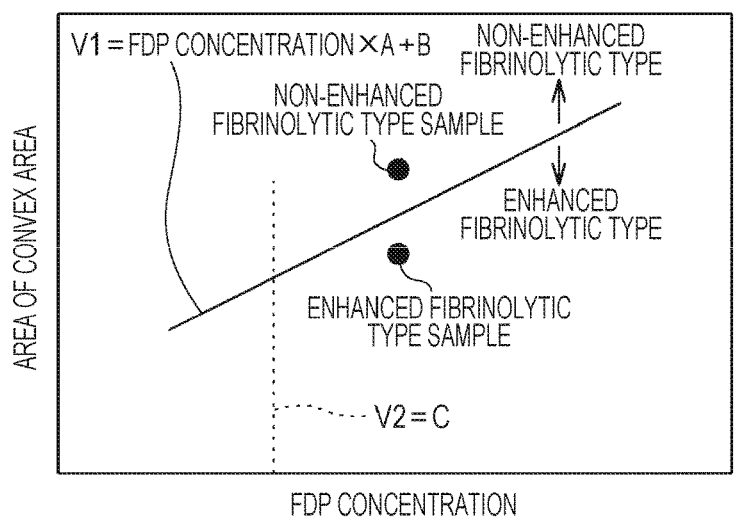
FIG. 5 is an explanatory view of an enhanced fibrinolytic state determination in a two-dimensional space of an FDP concentration and an area of a convex area.

The processing device 30 determines the enhanced fibrinolytic state based on the first information indicating the FDP concentration, and the second information indicating the curving degree of the time course curve. FIG. 5 shows a two-dimensional space in which the horizontal axis indicates the FDP concentration, and the vertical axis indicates the area of the convex area. The inventor of the present invention found that when the points specified by the first information and the second information are plotted in the two-dimensional space of FIG. 5, there is a difference between the distribution of points of the first information and the second information obtained from the enhanced fibrinolytic type sample, and the distribution of points of the first information and the second information obtained from the non-enhanced fibrinolytic type sample. In other words, the enhanced fibrinolytic type sample is basically distributed in a great amount on the lower right side of the two-dimensional space of FIG. 5, whereas the non-enhanced fibrinolytic type sample is basically distributed in a great amount on the left side or the upper left side of the two-dimensional space of FIG. 5.

Therefore, in the determination of the enhanced fibrinolytic state of the blood sample, the enhanced fibrinolytic state can be determined without obtaining the FDP/D dimer ratio as in the prior art as long as the FDP concentration and the area of the convex area are known. The determination of the enhanced fibrinolytic state of the blood sample may include a determination of comparing a value V1, obtained by applying the first information indicating the FDP concentration to an evaluation function, with the area of the convex area, which is the second information. The evaluation function is, for example, a function proportional to the FDP concentration, and is expressed as FDP concentration× A+B. In the formula, A and B are coefficients defined by the conditions for acquiring the time course curve. Examples of values for A and B will be described later. The condition of determination using the evaluation function is expressed by the following formula (2). Hereinafter, the determination by formula (2) is referred to as a first determination. Formula (2) including the evaluation function is stored in the memory 32 as the analysis information 32b.

[Formula 2]

$$\text{Area of convex area} \leq \text{FDP concentration} \times A + B \quad (2)$$

When the FDP concentration and the area of the convex area calculated by the processing device 30 are plotted in FIG. 5, the determination on whether or not formula (2) is satisfied is equivalent to the determination on whether or not the plotted points are located to coincide with a determination line V1=FDP concentration×A+B corresponding to formula (2) in FIG. 5 or below the determination line V1. The processing device 30 determines that the sample is of the enhanced fibrinolytic type when formula (2) is satisfied.

The determination of the enhanced fibrinolytic state of the blood sample may further include comparing the first information indicating the FDP concentration with a threshold value C. The threshold value C is a value determined in view of the strength to capture the enhanced fibrinolytic type sample in the FDP measuring reagent. The condition of determination using the threshold value C is expressed by the following formula (3). Hereinafter, the determination by formula (3) is referred to as a second determination. Formula (3) is stored in the memory 32 as the analysis information 32c.

[Formula 3]

$$\text{FDP concentration} \geq C \quad (3)$$

The processing device 30 determines that the sample is of the enhanced fibrinolytic type if formula (3) is also satisfied in addition to formula (2), so that the determination can be made more accurately.

The determination of the enhanced fibrinolytic state of the blood sample is not limited to that which uses the determination conditions expressed by formulae (2) and (3). For example, an area to which the enhanced fibrinolytic type sample is to belong in the two-dimensional space shown in FIG. 5 may be sectionalized in advance, and the determination may be made from whether or not a two-dimensional spatial coordinate indicated by the first information and the second information obtained from the sample to be analyzed belongs to the relevant area to which the enhanced fibrinolytic type sample is to belong.

2.6 Setting Example of Coefficients A and B, and Threshold Value C

2.6.1 Verification Result of First Setting Example and Determination Performance In a first setting example, only the first determination expressed by formula (2) is carried out for the determination of the enhanced fibrinolytic state of a case where the area of the convex area is used. Therefore, the values set in the first setting example are the coefficients A and B, and the threshold value C is not set. The D dimer measurement is also carried out in addition to the FDP measurement for the verification of the determination performance in the first setting example. For the verification of the determination performance of the first setting example, sensitivity and specificity in the first setting example were obtained in the comparison with the determination result of the enhanced fibrinolytic state of a case where the FDP/D dimer ratio was used. The blood sample used for the verification of the first setting example is a frozen blood plasma sample, and 37 cases in total are provided.

The FDP measurement specimen was prepared by mixing the FDP measuring reagent in the sample. The FDP measuring reagent used is LIAS AUTO P-FDP reagent manufactured by Sysmex Corporation. The sample whose FDP concentration exceeds 120 μg/mL was subjected to 8-fold dilution measurement with a diluent of fibrinolytic system manufactured by Sysmex Corporation, and the area of the convex area was obtained by octuplicating the value obtained by formula (1).

The D dimer measurement specimen was prepared by mixing the D dimer measuring reagent in the sample. The D dimer measuring reagent used is D dimer measurement kit, LIAS AUTO D-dimer NEO manufactured by Sysmex Corporation.

For the verification of the determination performance in the first setting example, the FDP measurement specimen and the D dimer measurement specimen prepared as described above are each measured with a fully automatic blood coagulation measuring device CS 2000i manufactured by Sysmex Corporation to obtain a time course curve of the OD value of each measurement specimen. The FDP concentration and the D dimer concentration were calculated from the obtained time course curve according to the attached document of the used specimen. The FDP/D dimer ratio, which is the ratio between the FDP concentration and the D dimer concentration, was calculated from the FDP concentration and the D dimer concentration.

In the first setting example and a second setting example to be described later, a criterion for determining that FDP/D dimer ratio ≥2.5 is positive, that is, enhanced fibrinolytic state is adopted for the determination criterion of the enhanced fibrinolytic state of a case where the FDP/D dimer ratio is used, and the magnitude of the FDP concentration is not taken into consideration.

Figure 6:
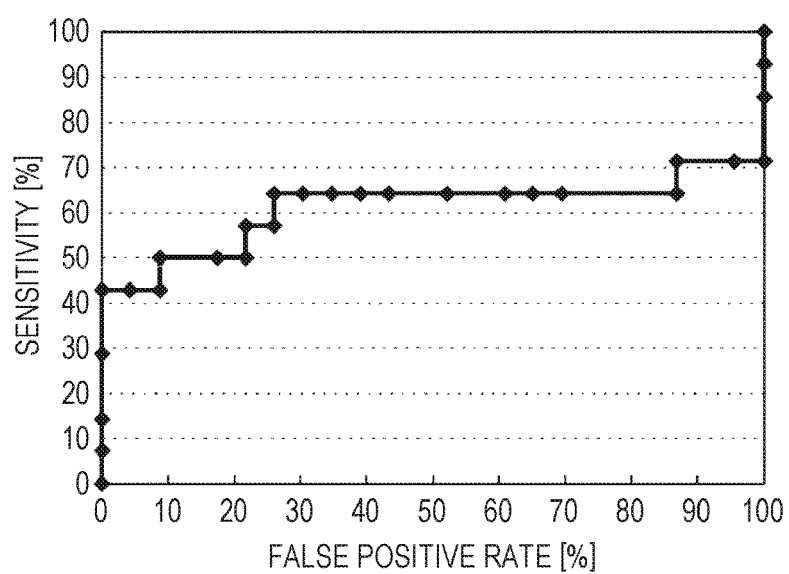
FIG. 6 is an ROC curve in a first setting example.

For the determination of the enhanced fibrinolytic state when the area of the convex area is used, the area of the convex area was obtained by formula (1) from the time course curve of the OD value of the FDP measurement specimen. For the determination of the enhanced fibrinolytic state of a case where the area of the convex area is used, the first determination expressed by formula (2) was carried out to obtain an ROC curve shown in FIG. 6. The ROC curve of FIG. 6 is an ROC curve of a case where the coefficient B, of the coefficients A and B included in the evaluation function on the right side of formula (2), was set to −2.6, and the coefficient A was changed within a range from 2.0 to 0.0. In FIG. 6, the horizontal axis indicates a false positive rate, and the vertical axis indicates the sensitivity. The area below the ROC curve of the ROC curve of FIG. 6 is 0.61.

The value of the coefficient A was determined from the ROC curve of FIG. 6. The determined value of the coefficient A is a value of the coefficient A at a point most distant toward the upper left side from a line connecting a point of (false positive rate, sensitivity)=(0%, 0%) with a point of (false positive rate, sensitivity)=(100%, 100%) in the ROC curve of FIG. 6. Here, A=0.29.

The following Table 1 shows the determination result of the enhanced fibrinolytic type state obtained by comparing the value V1, obtained by substituting the calculated FDP concentration in the evaluation function in which A=0.29 and B=−2.6, with the area of the convex area.

TABLE 1

| | Enhanced fibrinolytic type (determination by FDP/DD) | Non-enhanced fibrinolytic type (determination by FDP/DD) | Total |
|---|---|---|---|
| Enhanced fibrinolytic type (First determination alone) | 9 samples | 6 samples | 15 samples |
| Non-enhanced fibrinolytic type (First determination alone) | 5 samples | 17 samples | 22 samples |
| Total | 14 samples | 23 samples | 37 samples |

Figure 7:
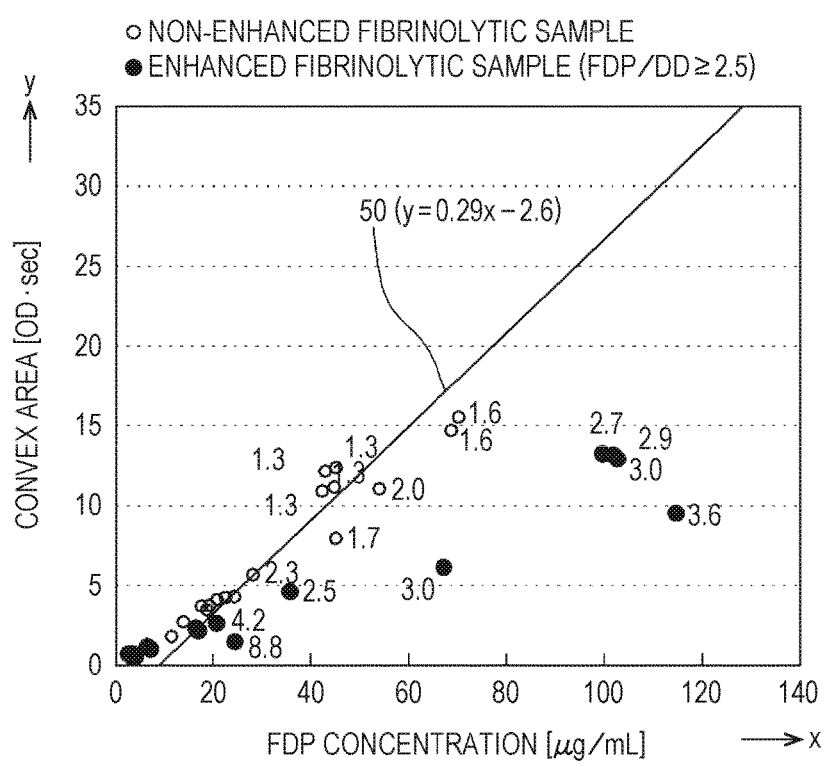
FIG. 7 is a graph showing plotting results and an enhanced fibrinolytic determination line in the first setting example.

FIG. 7 shows the result of plotting the FDP concentration and the area of the convex area obtained from the FDP measurement specimen of each of the 37 samples. In FIG. 7, white circle plots indicate those determined as the non-enhanced fibrinolytic samples according to the determination of the enhanced fibrinolytic state of a case where the FDP/D dimer ratio is used, and black circle plots indicate those determined as the enhanced fibrinolytic samples according to the determination of the enhanced fibrinolytic state of a case where the FDP/D dimer ratio is used. The numerical value near the plot indicates the FDP/D dimer ratio calculated from the FDP concentration and the D dimer concentration. In FIG. 7, a determination line 50 corresponding to the evaluation function of the right side of formula (2) is shown. The determination line 50 of FIG. 7 corresponds to the evaluation function in which A=0.29 and B=−2.6. In FIG. 7, the plots that coincide with the determination line 50 and the plots below the determination line 50 are determined as of the enhanced fibrinolytic type according to the first determination expressed by formula (2).

As is apparent from Table 1 and FIG. 7, the number of samples determined as of the enhanced fibrinolytic type by the first determination expressed by formula (2) is 15, and the number of samples determined as of the non-enhanced fibrinolytic type is 22. On the other hand, the number of samples determined as of the enhanced fibrinolytic type by the determination of the enhanced fibrinolytic state of a case where the FDP/D dimer ratio is used is 14, and the number of samples determined as of the non-enhanced fibrinolytic type is 23. According to Table 1, the true positive samples are 9 cases, the false positive samples are 6 cases, the false negative samples are 5 cases, and the true negative samples are 17 cases.

According to the first setting example, sensitivity of the enhanced fibrinolytic state determination by the first determination expressed by formula (2)=true positive sample (9 cases)/positive sample (14 cases)=64%, specificity=true negative sample (17 cases)/negative sample (23 cases)=74%.

2.6.2 Verification Result of Second Setting Example and Determination Performance Similarly to the first setting example, in the second setting example as well, only the first determination expressed by formula (2) is carried out for the determination of the enhanced fibrinolytic state of a case where the area of the convex area is used. Therefore, the values set in the second setting example are also the coefficients A and B.

The difference between the first setting example and the second setting example is that the blood sample is a frozen blood plasma sample in the first setting example, whereas the blood sample is a fresh blood plasma sample in the second setting example. In the second setting example, 54 fresh blood plasma samples were used. In the second setting example, the FDP measurement specimen and the D dimer measurement specimen were respectively measured by the Fully Automated Blood Coagulation Analyzer CS5100 manufactured by Sysmex Corporation to obtain a time course curve of the OD value of each measurement specimen. The FDP concentration and the D dimer concentration were calculated from the obtained time course curve according to the attached document of the used specimen. The FDP/D dimer ratio, which is the ratio between the FDP concentration and the D dimer concentration, was calculated from the FDP concentration and the D dimer concentration. The FDP/D dimer ratio is calculated by FDP concentration/D dimer concentration.

Figure 8:
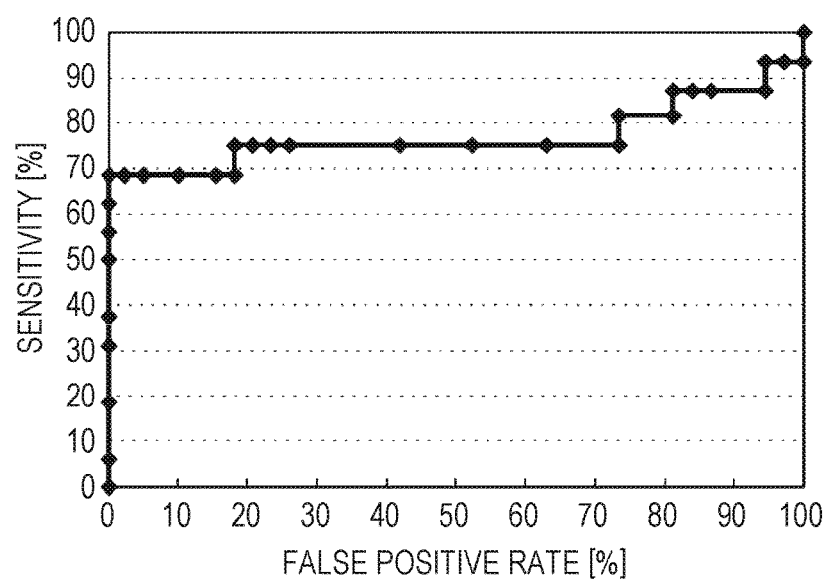
FIG. 8 is an ROC curve in a second setting example.

In the second setting example, the determination performance was verified under the conditions similar to those in the first setting example. The first determination expressed by formula (2) was carried out for the determination of the enhanced fibrinolytic state of a case where the calculated area of the convex area was used to obtain the ROC curve shown in FIG. 8. The ROC curve of FIG. 8 is an ROC curve of a case where the coefficient B, of the coefficients A and B included in the evaluation function of the right side of formula (2), was set to −2.6, and the coefficient A was changed within a range from 2.0 to 0.0. In FIG. 8, the horizontal axis indicates a false positive rate, and the vertical axis indicates the sensitivity. The area below the ROC curve of the ROC curve of FIG. 8 is 0.77.

Similarly to the first setting example, the value of the coefficient A was determined from the ROC curve of FIG. 8. Here, A=0.29.

The following Table 2 shows the determination result of the enhanced fibrinolytic type state obtained by comparing the value V1, which is obtained by substituting the calculated FDP concentration in the evaluation function in which A=0.29 and B=−2.6, with the area of the convex area.

TABLE 2

|  | Enhanced fibrinolytic type (determination by FDP/DD) | Non-enhanced fibrinolytic type (determination by FDP/DD) | Total |
|---|---|---|---|
| Enhanced fibrinolytic type (First determination alone) | 12 samples | 8 samples | 20 samples |
| Non-enhanced fibrinolytic type (First determination alone) | 4 samples | 30 samples | 34 samples |
| Total | 16 samples | 38 samples | 54 samples |

Figure 9:
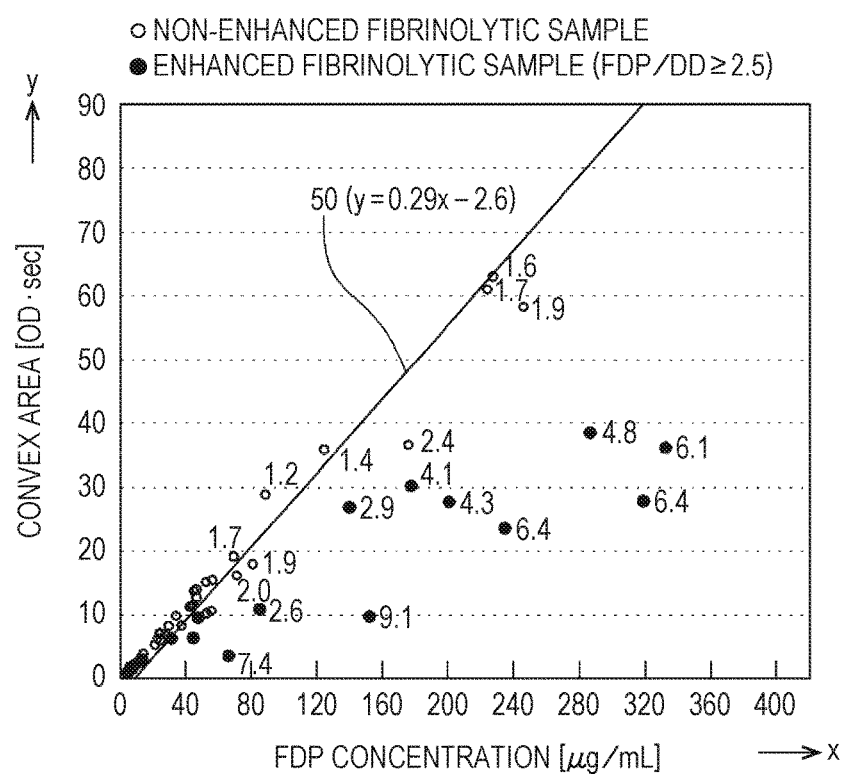
FIG. 9 is a graph showing plotting results and an enhanced fibrinolytic determination line in the second setting example.

FIG. 9 shows the result of plotting the FDP concentration and the area of the convex area obtained from the FDP measurement specimen of each of the 54 samples. In FIG. 9, the white circle plots indicate those determined as the non-enhanced fibrinolytic samples according to the determination of the enhanced fibrinolytic state of a case where the FDP/D dimer ratio is used, and black circle plots indicate those determined as the enhanced fibrinolytic samples according to the determination of the enhanced fibrinolytic state of a case where the FDP/D dimer ratio is used. The numerical value near the plot indicates the FDP/D dimer ratio calculated from the FDP concentration and the D dimer concentration. In FIG. 9, a determination line 50 corresponding to the evaluation function of the right side of formula (2) is shown. The determination line 50 of FIG. 9 corresponds to the evaluation function in which A=0.29 and B=−2.6. In FIG. 9, the plots that coincide with the determination line 50 and the plots below the determination line 50 are determined as of the enhanced fibrinolytic type according to the first determination expressed by formula (2).

As is apparent from Table 2 and FIG. 9, the number of samples determined as of the enhanced fibrinolytic type by the first determination expressed by formula (2) is 20, and the number of samples determined as of the non-enhanced fibrinolytic type is 34. On the other hand, the number of samples determined as of the enhanced fibrinolytic type by the determination of the enhanced fibrinolytic state of a case where the FDP/D dimer ratio is used is 16, and the number of samples determined as of the non-enhanced fibrinolytic type is 38. According to Table 2, the true positive samples are 12 cases, the false positive samples are 8 cases, the false negative samples are 4 cases, and the true negative samples are 30 cases.

According to the second setting example, sensitivity=true positive sample (12 cases)/positive sample (16 cases)=75%, and specificity=true negative sample (40 cases)/negative sample (30 cases)=79%.

As is apparent from the first setting example and the second setting example, the enhanced fibrinolytic state determination by the first determination expressed by formula (2) gives satisfactory sensitivity and specificity of a certain extent regardless of whether the blood sample is a frozen sample or a fresh sample.

2.6.3 Verification Result of Third Setting Example and Determination Performance Similarly to the first setting example and the second setting example, in a third setting example as well, only the first determination expressed by formula (2) is carried out for the determination of the enhanced fibrinolytic state of a case where the area of the convex area is used. Therefore, the values determined for the third setting example are also the coefficients A and B.

The third setting example differs from the first setting example and the second setting example in the reagent used. The FDP measurement specimen used in the third setting example is LPIA PDP-P manufactured by LSI Medience Corporation. A sample whose FDP concentration exceeds 80 µg/mL was subjected to 8-fold dilution measurement with a common diluent II(S) manufactured by LSI Medience Corporation, and the area of the convex area was obtained by octuplicating the value obtained by formula (1).

The D dimer measurement specimen used in the third setting example is LPIA Ace D-D dimer II manufactured by LSI Medience Corporation.

In the third setting example, the FDP measurement specimen and the D dimer measurement specimen were respectively measured by the Fully Automated Blood Coagulation Analyzer CS5100 manufactured by Sysmex Corporation to obtain a time course curve of the OD value of each measurement specimen. The FDP concentration and the D dimer concentration were calculated from the obtained time course curve according to the attached document of the used specimen. The FDP/D dimer ratio, which is the ratio between the FDP concentration and the D dimer concentration, was calculated from the FDP concentration and the D dimer concentration.

The blood sample used in the third setting example is 62 fresh blood plasma samples. In the third setting example as well, the determination performance was verified under the conditions similar to those in the first setting example and the second setting example. However, in the third setting example, a criterion for determining that the FDP/D dimer ratio ≥2.0 is positive, that is, the enhanced fibrinolytic state is adopted for the determination criterion of the enhanced fibrinolytic state of a case where the FDP/D dimer ratio is used. In the third setting example as well, the magnitude of the FDP concentration is not taken into consideration.

Figure 10:
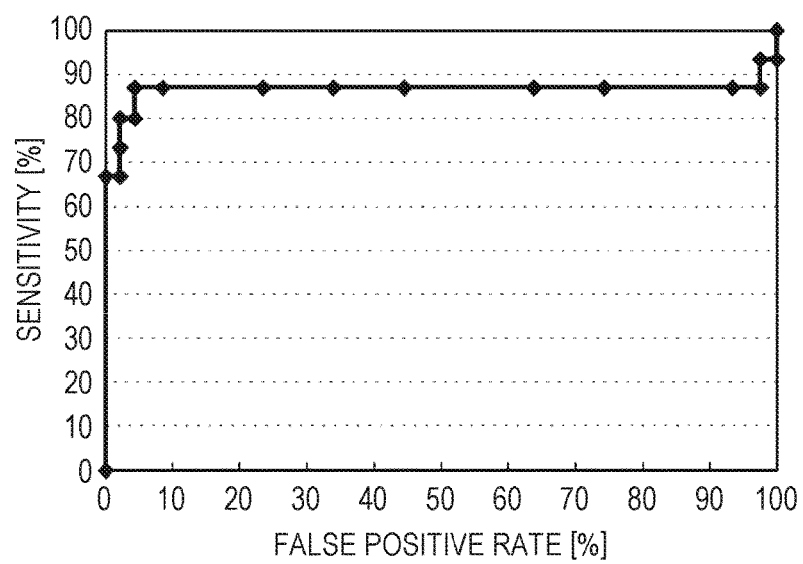
FIG. 10 is an ROC curve in a third setting example.

The first determination expressed by formula (2) was carried out for the determination of the enhanced fibrinolytic state of a case where the calculated area of the convex area was used to obtain the ROC curve shown in FIG. 10. The ROC curve of FIG. 10 is an ROC curve of a case where the coefficient B, of the coefficients A and B included in the evaluation function of the right side of formula (2), was set to −0.97, and the coefficient A was changed within a range from 2.0 to −1.0. In FIG. 10, the horizontal axis indicates the false positive rate, and the vertical axis indicates the sensitivity. The area below the ROC curve of the ROC curve of FIG. 10 is 0.86.

Similarly to the first setting example and the second setting example, the value of the coefficient A was determined from the ROC curve of FIG. 10. Here, A=0.088.

The following Table 3 shows the determination result of the enhanced fibrinolytic type state obtained by comparing the value V1, obtained by substituting the calculated FDP concentration in the evaluation function in which A=0.088 and B=−0.97, with the area of the convex area.

TABLE 3

|  | Enhanced fibrinolytic type (determination by FDP/DD) | Non-enhanced fibrinolytic type (determination by FDP/DD) | Total |
|---|---|---|---|
| Enhanced fibrinolytic type (First determination alone) | 13 samples | 2 samples | 15 samples |
| Non-enhanced fibrinolytic type (First determination alone) | 2 samples | 45 samples | 47 samples |
| Total | 15 samples | 47 samples | 62 samples |

Figure 11:
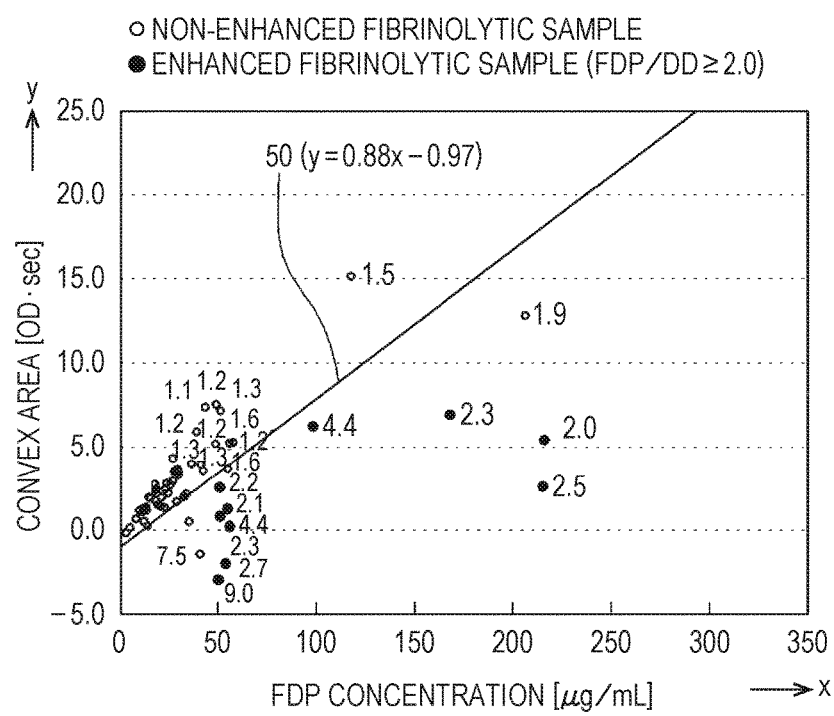
FIG. 11 is a graph showing plotting results and an enhanced fibrinolytic determination line in the third setting example.

FIG. 11 shows the result of plotting the FDP concentration and the area of the convex area obtained from the FDP measurement specimen of each of the 62 samples. In FIG. 11, the white circle plots indicate those determined as the non-enhanced fibrinolytic samples according to the determination of the enhanced fibrinolytic state of a case where the FDP/D dimer ratio is used, and black circle plots indicate those determined as the enhanced fibrinolytic samples according to the determination of the enhanced fibrinolytic state of a case where the FDP/D dimer ratio is used. The numerical value near the plot indicates the FDP/D dimer ratio calculated from the FDP concentration and the D dimer concentration. In FIG. 11, a determination line 50 corresponding to the evaluation function of the right side of formula (2) is shown. The determination line 50 of FIG. 11 corresponds to the evaluation function in which A=0.0887 and B=−0.97. In FIG. 11, the plots that coincide with the determination line 50 and the plots below the determination line 50 are determined as of the enhanced fibrinolytic type according to the first determination expressed by formula (2).

As is apparent from Table 3 and FIG. 11, the number of samples determined as of the enhanced fibrinolytic type by the first determination expressed by formula (2) is 15, and the number of samples determined as of the non-enhanced fibrinolytic type is 47. On the other hand, the number of samples determined as of the enhanced fibrinolytic type by the determination of the enhanced fibrinolytic state of a case where the FDP/D dimer ratio is used is 15, and the number of samples determined as of the non-enhanced fibrinolytic type is 47. According to Table 3, the true positive samples are 13 cases, the false positive samples are 2 cases, the false negative samples are 2 cases, and the true negative samples are 45 cases.

According to the third setting example, sensitivity=true positive sample (13 cases)/positive sample (15 cases)=87%, and specificity=true negative sample (45 cases)/negative sample (47 cases)=96%.

According to the first setting example to the third setting example, it is apparent that the determination of the enhanced fibrinolytic state by the first determination expressed by formula (2) is useful regardless of the FDP measuring reagent used.

2.6.4 Verification Result of Fourth Setting Example and Determination Performance In a fourth setting example, the second determination expressed by formula (3) is carried out in addition to the first determination expressed by formula (2) for the determination of the enhanced fibrinolytic state of a case where the area of the convex area is used, and the sample is determined as of the enhanced fibrinolytic type when formula (3) is also satisfied in addition to formula (2). Therefore, the values set in the fourth setting example are the coefficients A and B, and the threshold value C. In the fourth setting example, the measurement results of the 37 samples obtained in the first setting example are used to carry out the determination of the enhanced fibrinolytic state by the first determination and the second determination. In the fourth setting example, coefficient B=−2.6, and threshold value C=80 µg/mL.

Figure 12:
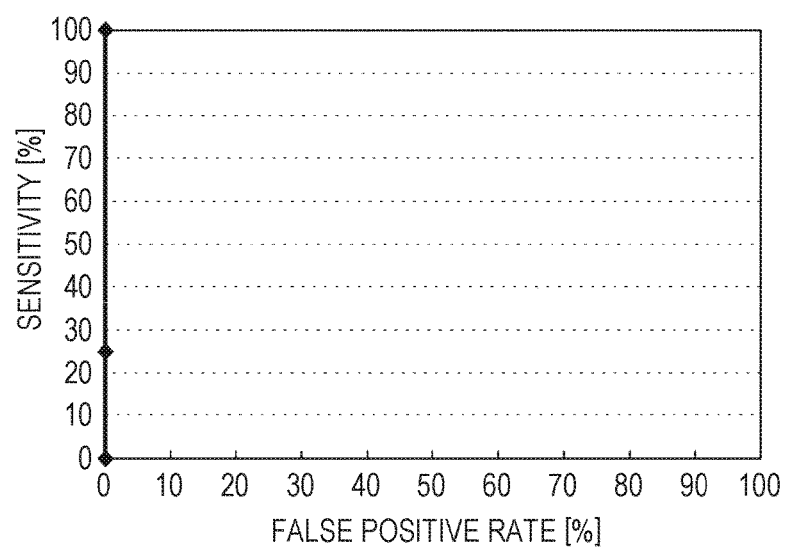
FIG. 12 is an ROC curve in a fourth setting example.
Figure 14:
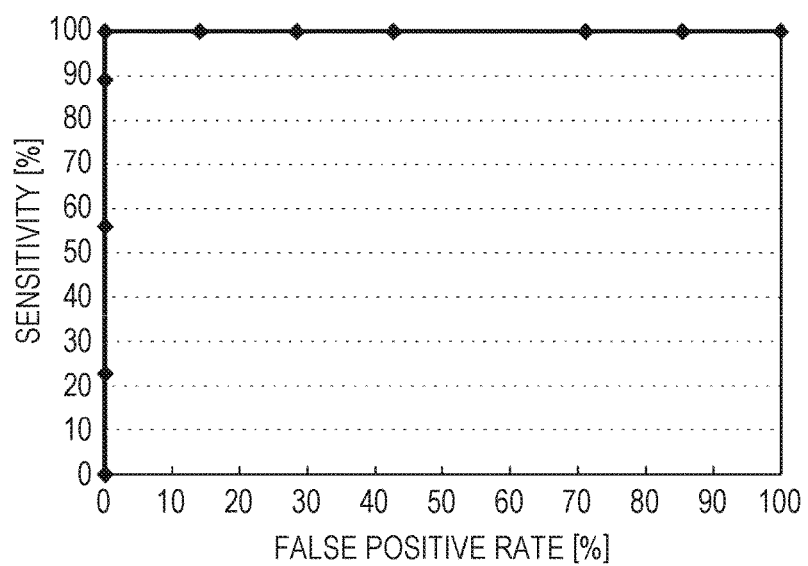
FIG. 14 is an ROC curve in a fifth setting example.

The ROC curve shown in FIG. 12 was obtained to determine the coefficient A in the fourth setting example. The ROC curve of FIG. 12 is an ROC curve of a case where the coefficient A of formula (2) was changed within a range from 2.0 to −1.0. In FIG. 12, the horizontal axis indicates the false positive rate, and the vertical axis indicates the sensitivity. The area below the ROC curve of the ROC curve of FIG. 14 is 1.0. Similarly to the first setting example, the value of the coefficient A was determined from the ROC curve of FIG. 12. Here, A=0.186.

In the fourth setting example and a fifth setting example to be described later, a criterion for determining that FDP/D dimer ratio ≥2.5 and FDP concentration≥80 µg/mL are positive, that is, enhanced fibrinolytic state is adopted for the determination criterion of the enhanced fibrinolytic state when the FDP/D dimer ratio is used.

The following Table 4 shows the determination result of the enhanced fibrinolytic type state obtained by the first determination and the second determination. The first determination is carried out by comparing the value V1, obtained by substituting the calculated FDP concentration in the evaluation function in which A=0.186 and B=−2.6, with the area of the convex area.

TABLE 4

|  | Enhanced fibrinolytic type (determination by FDP/DD) | Non-enhanced fibrinolytic type (determination by FDP/DD) | Total |
|---|---|---|---|
| Enhanced fibrinolytic type (first determination + second determination) | 4 samples | 0 samples | 4 samples |
| Non-enhanced fibrinolytic type (first determination + second determination) | 0 samples | 33 samples | 33 samples |
| Total | 4 samples | 33 samples | 37 samples |

Figure 13:
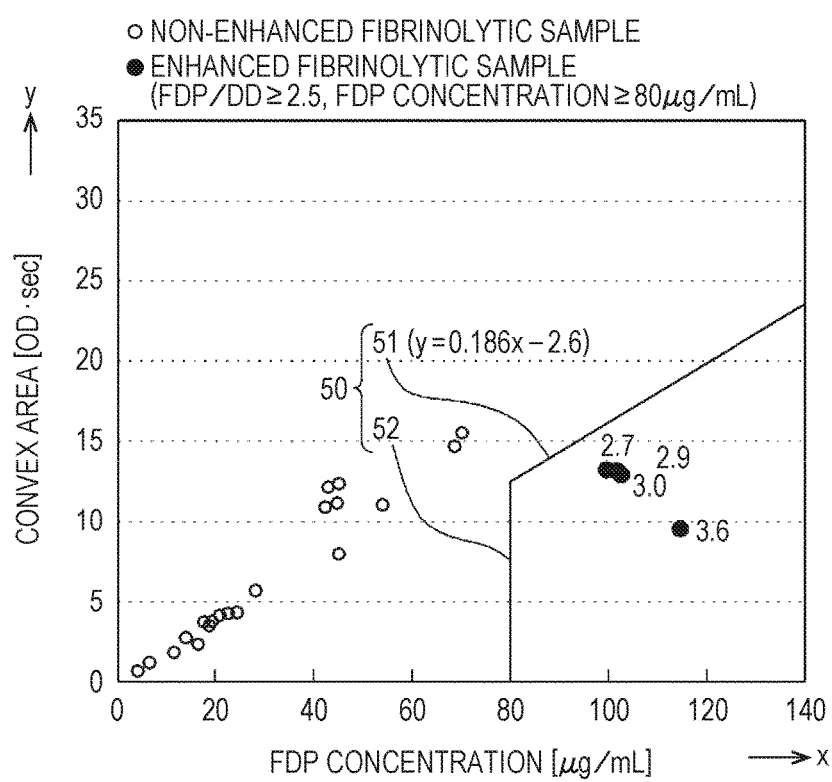
FIG. 13 is a graph showing plotting results and an enhanced fibrinolytic determination line in the fourth setting example.

FIG. 13 shows the determination line 50 according to the fourth setting example drawn in the plotting result similar to FIG. 7. The determination line 50 of FIG. 13 includes a first portion line 51 corresponding to the first determination expressed by formula (2), and a second portion line 52 corresponding to the second determination expressed by formula (3). In FIG. 13, the plot coinciding with the first portion line 51, the plot below the first portion line 51 and coinciding with the second portion line 52, and the plot on the right side of the second portion line 52 are determined as of the enhanced fibrinolytic type by the first determination and the second determination. As shown in FIG. 13, in the fourth setting example, the coefficient A is smaller than in the first setting example shown in FIG. 7. When the coefficient A is small, the sensitivity and the specificity may become lower than those in the first setting example if only the first determination expressed by formula (2) is carried out. However, more satisfactory sensitivity and specificity than in the first setting example can be obtained by also carrying out the second determination expressed by formula (3) even if the coefficient A is small. Therefore, the degree of freedom in the setting of the coefficient A can be enhanced by introducing the second determination. Similarly, the degree of freedom in the setting of the coefficient B can be enhanced by introducing the second determination.

As is apparent from Table 4 and FIG. 13, the number of samples determined as of the enhanced fibrinolytic type by the first determination expressed by formula (2) is 4, and the number of samples determined as of the non-enhanced fibrinolytic type is 33. On the other hand, the number of samples determined as of the enhanced fibrinolytic type by the determination of the enhanced fibrinolytic state of a case where the FDP/D dimer ratio is used is 4, and the number of samples determined as of the non-enhanced fibrinolytic type is 33. According to Table 4, the true positive samples are 4 cases, the false positive samples are 0 cases, the false negative samples are 0 cases, and the true negative samples are 33 cases.

According to the fourth setting example, sensitivity of the enhanced fibrinolytic state determination by the first determination expressed by formula (2)=true positive sample (4 cases)/positive sample (4 cases)=100%, specificity=true negative sample (33 cases)/negative sample (33 cases)= 100%.

2.6.5 Verification Result of Fifth Setting Example and Determination Performance In a fifth setting example, the measurement results of the 54 samples obtained in the second setting example are used to carry out the determination of the enhanced fibrinolytic state by the first determination and the second determination, similarly to the fourth setting example. In the fifth setting example, coefficient B=−2.6, and threshold value C=80 μg/mL.

The ROC curve shown in FIG. 14 was obtained to determine the coefficient A in the fifth setting example. The ROC curve of FIG. 14 is an ROC curve of a case where the coefficient A of formula (2) was changed within a range from 2.0 to −1.0. In FIG. 14, the horizontal axis indicates the false positive rate, and the vertical axis indicates the sensitivity. The area below the ROC curve of the ROC curve of FIG. 14 is 1.0.

Similarly to the first setting example, the value of the coefficient A was determined from the ROC curve of FIG. 14. Here, A=0.22.

The following Table 5 shows the determination result of the enhanced fibrinolytic type state obtained by the first determination and the second determination. The first determination is carried out by comparing the value V1, obtained by substituting the calculated FDP concentration in the evaluation function in which A=0.22 and B=−2.6, with the area of the convex area. In the determination of Table 5, 16 samples excluding the 38 samples, in which the FDP concentration is lower than 80 μg/mL, of the 54 samples are the determination target.

TABLE 5

|  | Enhanced fibrinolytic type (determination by FDP/DD) | Non-enhanced fibrinolytic type (determination by FDP/DD) | Total |
|---|---|---|---|
| Enhanced fibrinolytic type (first determination + second determination) | 9 samples | 0 samples | 9 samples |
| Non-enhanced fibrinolytic type (first determination + second determination) | 0 samples | 7 samples | 7 samples |
| Total | 9 samples | 7 samples | 16 samples |

Figure 15:
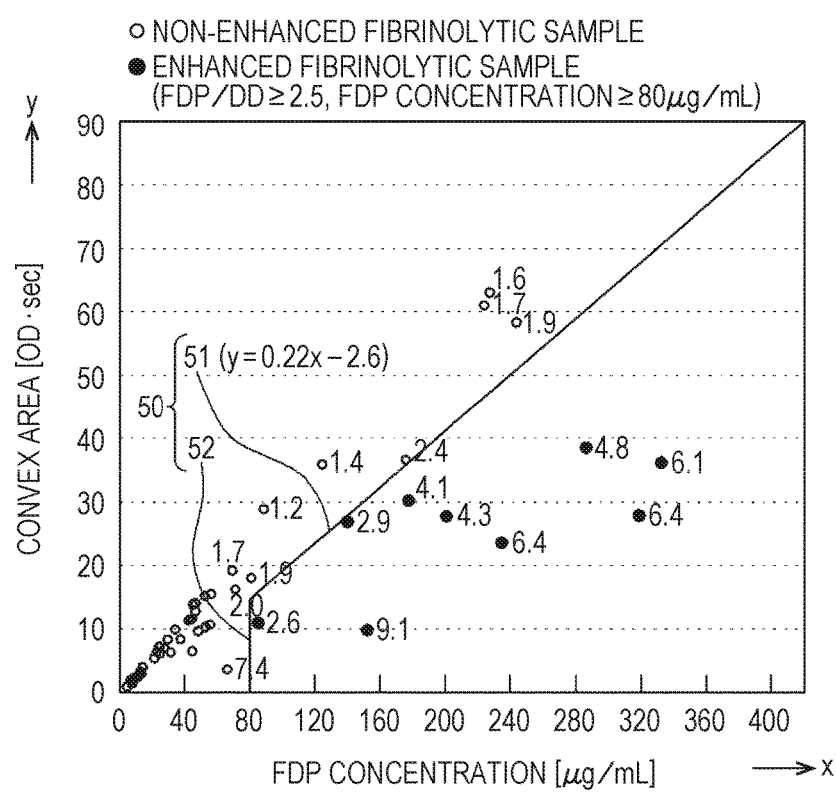
FIG. 15 is a graph showing plotting results and an enhanced fibrinolytic determination line in the fifth setting example.

FIG. 15 shows the determination line 50 according to the fifth setting example drawn in the plotting result similar to FIG. 9. The determination line 50 of FIG. 15 includes the first portion line 51 corresponding to the first determination expressed by formula (2), and the second portion line 52 corresponding to the second determination expressed by formula (3). In FIG. 15, the plot coinciding with the first portion line 51, the plot below the first portion line 51 and coinciding with the second portion line 52, and the plot on the right side of the second portion line 52 are determined as of the enhanced fibrinolytic type by the first determination and the second determination. As is apparent from Table 5 and FIG. 15, the number of samples determined as of the enhanced fibrinolytic type by the first determination expressed by formula (2) and the second determination expressed by formula (3) is 9, and the number of samples determined as of the non-enhanced fibrinolytic type is 7. On the other hand, the number of samples determined as of the enhanced fibrinolytic type by the determination of the enhanced fibrinolytic state of a case where the FDP/D dimer ratio is used is 9, and the number of samples determined as of the non-enhanced fibrinolytic type is 7. According to Table 5, the true positive samples are 9 cases, the false positive samples are 0 cases, the false negative samples are 0 cases, and the true negative samples are 7 cases.

According to the fifth setting example, sensitivity of the enhanced fibrinolytic state determination by the first determination and the second determination=true positive sample (9 cases)/positive sample (9 cases)=100%, specificity=true negative sample (7 cases)/negative sample (7 cases)=100%. Thus, in the fifth setting example, the determination performance is enhanced compared to the second setting example by also carrying out the second determination.

2.6.6 Verification Result of Sixth Setting Example and Determination Performance In a sixth setting example, the measurement results of the 62 samples obtained in the third setting example are used to carry out the determination of the enhanced fibrinolytic state by the first determination and the second determination, similarly to the fourth setting example and the fifth setting example. In the sixth setting example, however, a criterion for determining that FDP/D dimer ratio ≥2.0 and FDP concentration≥50 μg/mL are positive, that is, enhanced fibrinolytic state is adopted for the determination criterion of the enhanced fibrinolytic state of a case where the FDP/D dimer ratio is used.

Figure 16:
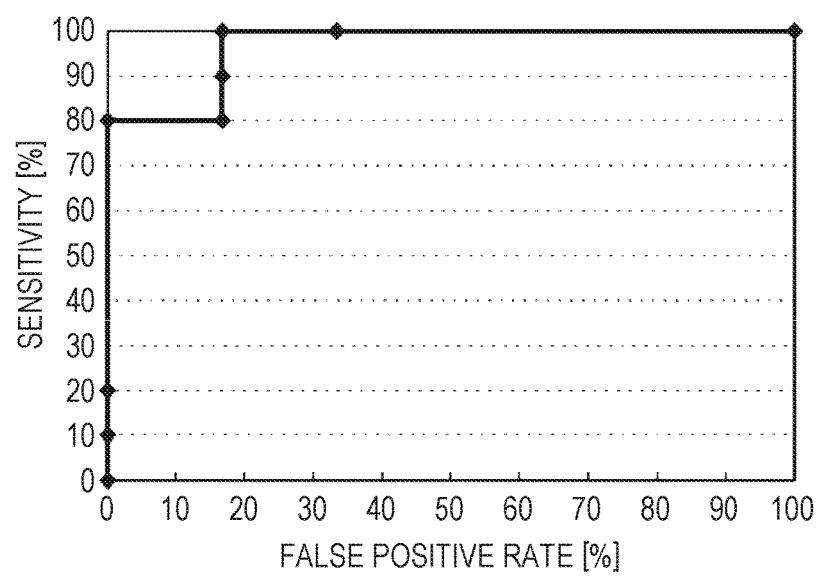
FIG. 16 is an ROC curve in a sixth setting example.

In the sixth setting example, coefficient B=−0.97, and threshold value C=50 μg/mL are used. The ROC curve shown in FIG. 16 was obtained to determine the coefficient A in the sixth setting example. The ROC curve of FIG. 16 is an ROC curve of a case where the coefficient A of formula (2) was changed within a range from 2.0 to −1.0. In FIG. 16, the horizontal axis indicates the false positive rate, and the vertical axis indicates the sensitivity. The area below the ROC curve of the ROC curve of FIG. 16 is 0.97.

Similarly to the first setting example, the value of the coefficient A was determined from the ROC curve of FIG. 16. Here, A=0.076.

The following Table 6 shows the determination result of the enhanced fibrinolytic type state obtained by the first determination and the second determination. The first determination is carried out by comparing the value V1, obtained by substituting the calculated FDP concentration in the evaluation function in which A=0.076 and B=−0.97, with the area of the convex area. In the determination of Table 6, 16 samples excluding the 46 samples, in which the FDP concentration is lower than 50 μg/mL, of the 62 samples are the determination target.

TABLE 6

|  | Enhanced fibrinolytic type (determination by FDP/DD) | Non-enhanced fibrinolytic type (determination by FDP/DD) | Total |
|---|---|---|---|
| Enhanced fibrinolytic type (first determination + second determination) | 10 samples | 1 sample | 11 samples |
| Non-enhanced fibrinolytic type (first determination + second determination) | 0 samples | 5 samples | 5 samples |
| Total | 10 samples | 6 samples | 16 samples |

Figure 17:
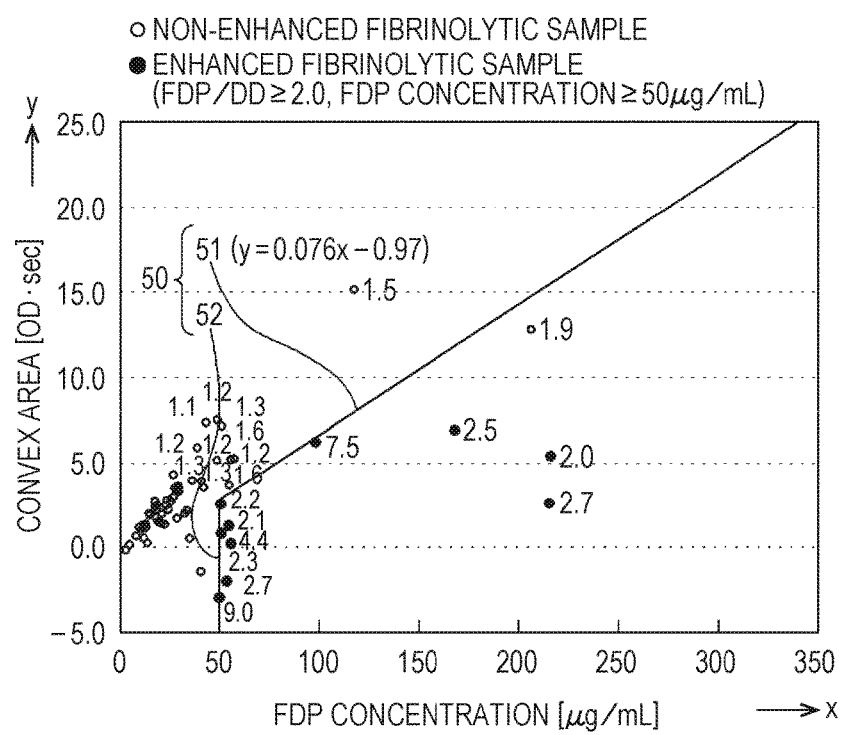
FIG. 17 is a graph showing plotting results and an enhanced fibrinolytic determination line in the sixth setting example.

FIG. 17 shows a determination line according to the sixth setting example drawn in the plotting result similar to FIG. 11. The determination line 50 of FIG. 17 includes the first portion line 51 corresponding to the first determination expressed by formula (2), and the second portion line 52 corresponding to the second determination expressed by formula (3). In FIG. 17, the plot coinciding with the first portion line 51, the plot below the first portion line 51 and coinciding with the second portion line 52, and the plot on the right side of the second portion line 52 are determined as of the enhanced fibrinolytic type by the first determination and the second determination. As is apparent from Table 6 and FIG. 17, the number of samples determined as of the enhanced fibrinolytic type by the first determination expressed by formula (2) and the second determination expressed by formula (3) is 11, and the number of samples determined as of the non-enhanced fibrinolytic type is 5. On the other hand, the number of samples determined as of the enhanced fibrinolytic type by the determination of the enhanced fibrinolytic state of a case where the FDP/D dimer ratio is used is 10, and the number of samples determined as of the non-enhanced fibrinolytic type is 6. Therefore, the true positive samples are 10 cases, the false positive sample is 1 case, the false negative samples are 0 cases, and the true negative samples are 5 cases.

Therefore, according to the sixth setting example, sensitivity of the enhanced fibrinolytic state determination by the first determination and the second determination=true positive sample (10 cases)/positive sample (10 cases)=100%, specificity=true negative sample (5 cases)/negative sample (6 cases)=83%. Thus, in the sixth setting example, the determination performance is enhanced compared to the third setting example by also carrying out the second determination.

3. Verification 3.1 First Verification Experiment

A first verification experiment was conducted to verify the relationship between the FDP concentration used for the enhanced fibrinolytic state determination and the area of the convex area of the time course curve. In the first verification experiment, an artificial FDP specimen in which the FDP/D dimer ratio was adjusted to a predetermined value was diluted to prepare three types of verifying samples each having an FDP concentration of 30 μg/mL, 60 μg/mL, and 120 μg/mL. For the artificial FDP specimen, a PD-FDP standard product manufactured by Sysmex Corporation adjusted to FDP/D dimer ratio=2 was used. The diluent of fibrinolytic system manufactured by Sysmex Corporation was used to dilute the artificial FDP specimen. Each of the three verifying samples having different FDP concentrations was mixed with LIAS AUTO P-FDP, which is the FDP measuring reagent manufactured by Sysmex Corporation, to prepare three measurement specimens. The three measurement specimens have the same FDP/D dimer ratio but different FDP concentrations.

Figure 18:
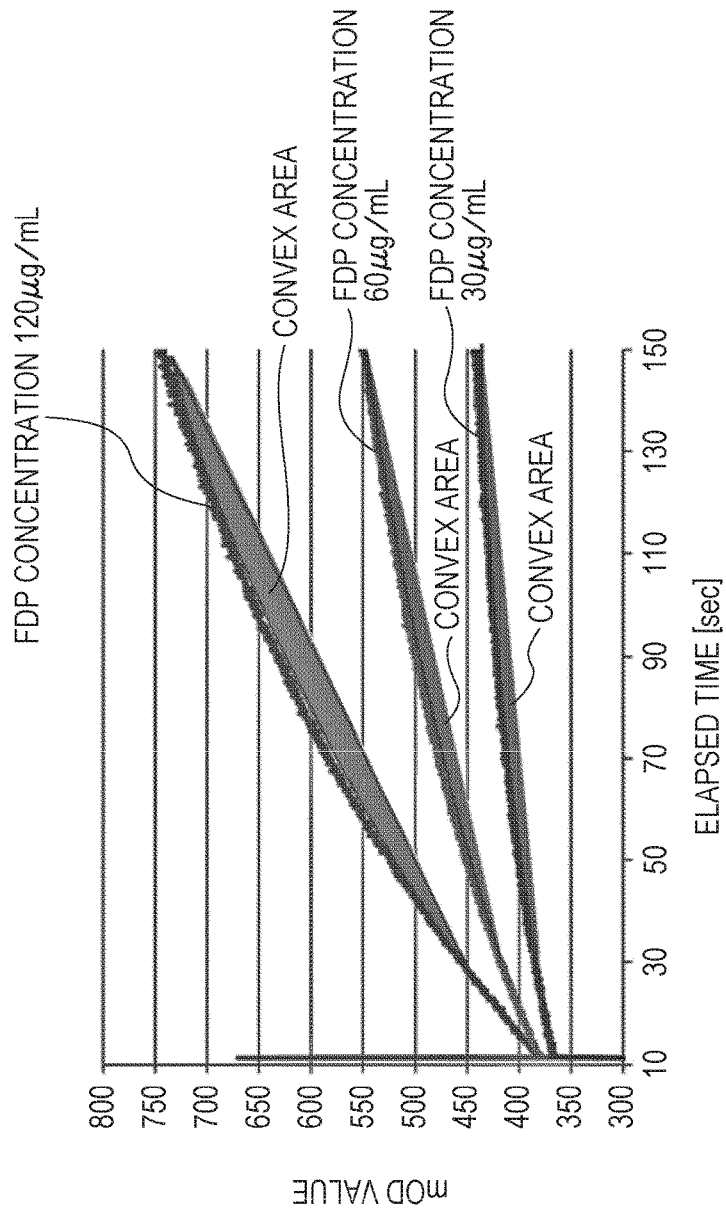
FIG. 18 is a graph showing a relationship between the FDP concentration and the area of the convex area.

The three measurement specimens were measured by the Fully Automated Blood Coagulation Analyzer CS2000i manufactured by Sysmex Corporation to obtain a time course curve of the OD value of each measurement specimen. FIG. 18 shows the time course curve obtained from the three measurement specimens having different FDP concentrations. According to the time course curve shown in FIG. 18, it can be seen that the curvature of the time course curve increases and the area of the convex area increases in proportion to the FDP concentration if the FDP/DD ratio is constant.

Through a method similar to the above, five types of verifying samples each having an FDP concentration of 5 μg/mL, 10 μg/mL, 30 μg/mL, 60 μg/mL, 80 μg/mL, or 120 μg/mL were prepared. Each of the five types of verifying samples was mixed with the LIAS AUTO P-FDP of three different lots to prepare a measurement specimen. Each of the three different lots is referred to as a first lot, a second lot, and a third lot. Each measurement specimen was measured similarly to the above to obtain a time course curve of each measurement specimen. The area of the convex area was calculated according to formula (1) from the obtained time course curve. As is apparent from FIGS. 19A to 19C in which the FDP concentration and the area of the convex area are plotted for each lot to draw the regression line, it can be seen that a linear relationship expressed by the formula: area of convex area=FDP concentration×A+B is established between the FDP concentration and the area of the convex area if the FDP/D dimer ratio is constant.

Figure 19A:
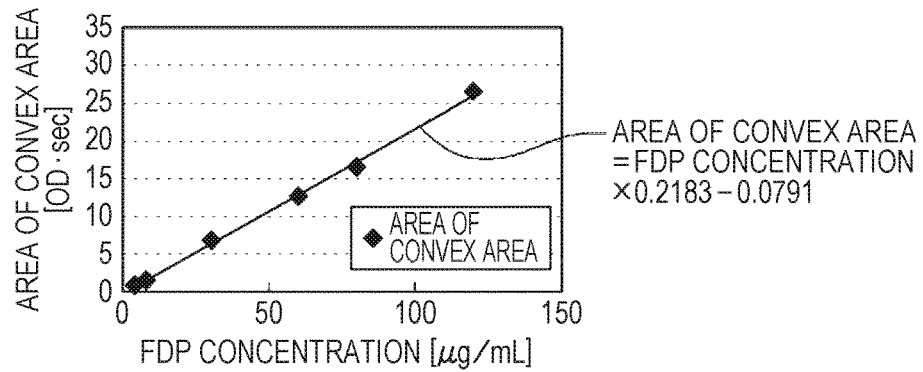
FIGS. 19A, 19B and 19C show graphs showing a relationship between the FDP concentration and the area of the convex area.
Figure 19B:
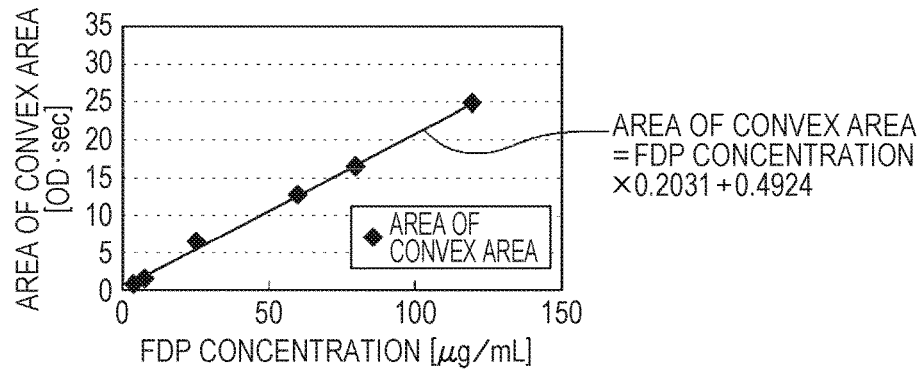
Figure 19C:
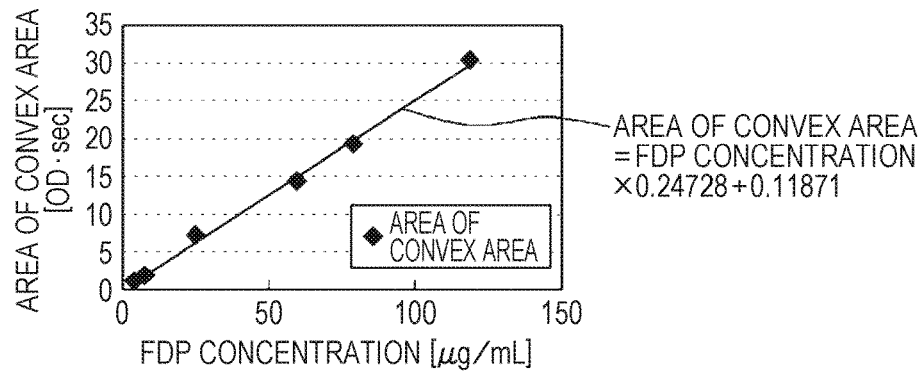

In FIG. 19A for the first lot, A=0.2183, B=−0.0791, and the correlation coefficient r was 0.9988. In FIG. 19B for the second lot, A=0.2031, B=0.4924, and the correlation coefficient r was 0.9983. In FIG. 19C for the third lot, A=0.24728, B=0.11871, and the correlation coefficient r was 0.9985.

3.2 Second Verification Experiment

A second verification experiment was conducted to verify the relationship between the FDP/D dimer ratio and the area of the convex area when the FDP concentration is constant. In the second verification experiment, three verifying samples each having a constant FDP concentration of 40 μg/mL, and an FDP/D dimer ratio of 1.0, 2.0, or 4.0 were prepared. The verifying samples were obtained by mixing an artificial D dimer specimen with an artificial fibrinogen decomposition product specimen. Each of the three verifying samples was mixed with LIAS AUTO P-FDP, which is the FDP measuring reagent manufactured by Sysmex Corporation, to prepare three measurement specimens. The three measurement specimens have the same FDP concentration but different FDP/D dimer ratios.

Figure 20A:
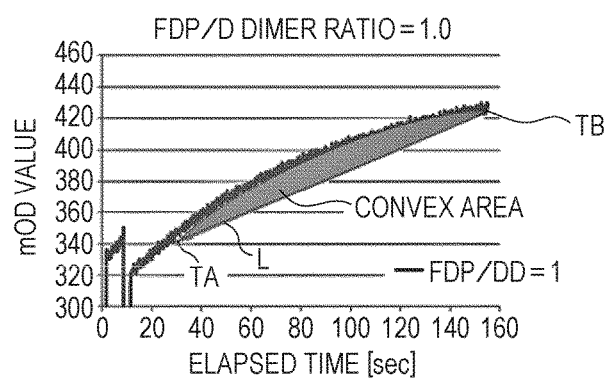
FIGS. 20A, 20B and 20C show graphs showing a relationship between an FDP/D dimer ratio and the area of the convex area.
Figure 20B:
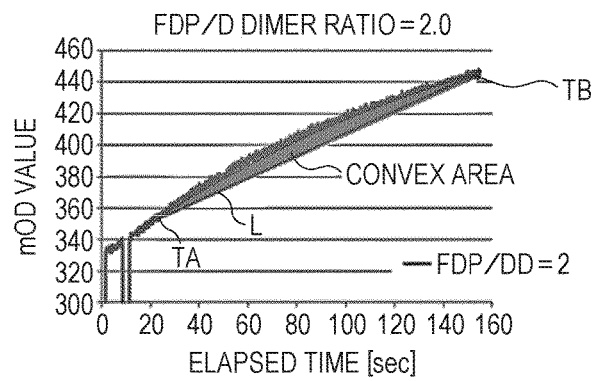
Figure 20C:
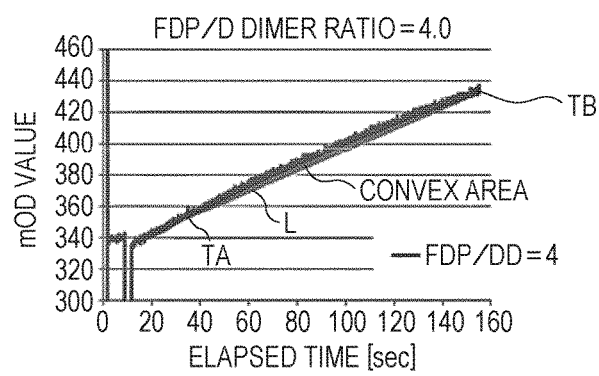

The three measurement specimens were measured by the Fully Automated Blood Coagulation Analyzer CS2000i manufactured by Sysmex Corporation to obtain a time course curve of the OD value of each measurement specimen. FIGS. 20A to 20C show the time course curves obtained from the three measurement specimens having different FDP/D dimer ratios. According to the time course curve shown in FIGS. 20A to 20C, it can be seen that the larger the FDP/D dimer ratio is, the more linear shape the time course curve shows and the more reduced is the curving degree. In other words, in the time course curve, it can be seen that the larger the FDP/D dimer ratio is, the more reduced is an area bulging out upward with respect to the line L connecting the starting point TA at the time point of 30 seconds with the terminating point TB at the time point of 150 seconds, that is, the area of the convex area.

Thus, the FDP/D dimer ratio can be predicted from the size of the area of the convex area. When the D dimer concentration is very small and the FDP/D dimer ratio is very large, the area may project out downward with respect to the line L, and in this case, the curving degree of the time course curve and the area of the convex area take negative values.

3.3 Consideration on First Verification Experiment and Second Verification Experiment According to the results of the first verification experiment and the second verification experiment, it can be confirmed that the FDP/D dimer ratio can be predicted by obtaining the FDP concentration and the area of the convex area. Therefore, formula (2) used for the first determination can be confirmed to be an alternative of the enhanced fibrinolytic state determination using the FDP/D dimer ratio. In other words, the enhanced fibrinolytic state determination can be carried out by obtaining the FDP concentration and the area of the convex area.

3.4 Verification by Western Blotting

Figure 21:
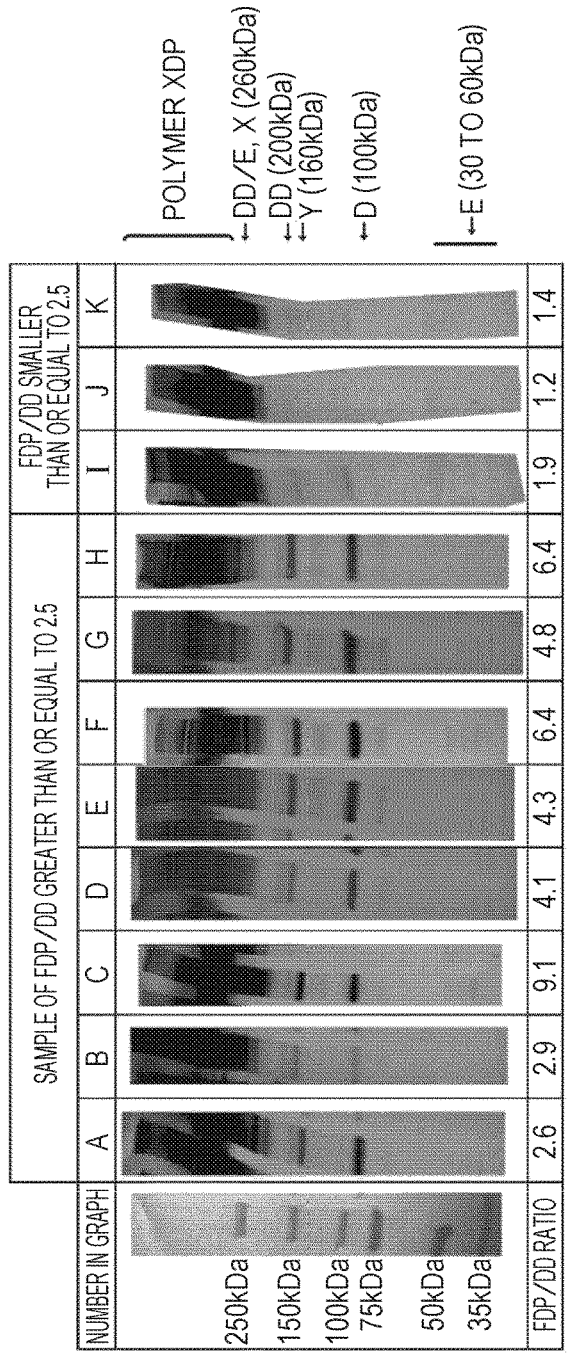
FIG. 21 is a diagram showing a result of Western blotting.

Among the total of 54 samples plotted in FIG. 15, 11 samples were verified by the Western blotting. The results are shown in FIG. 21.

Figure 22:
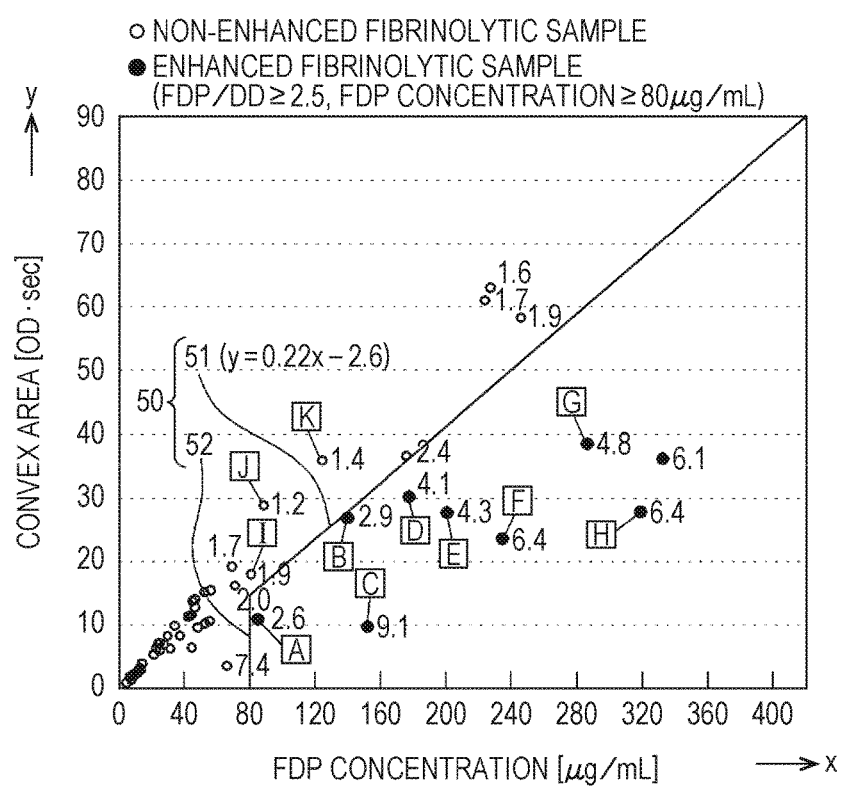
FIG. 22 is a graph showing samples A to K serving as verification targets by the Western blotting of the plotted points in FIG. 9.

The Western blotting was performed using the following.
Bio-Rad ReadyGel 5-20%
Dako Corporation A0080 antihuman fibrinogen polyclonal antibody (rabbit)
Dako Corporation P0448 antirabbit antibody-HRP (goat)
Dako Corporation antimouse antibody-HRP (rabbit)
Bio-Rad Corporation 170-6431 HRP Conjugate Substrate Kit The 11 samples serving as the verifying target of the Western blotting are indicated by alphabets A to K in FIG. 22. In FIG. 22 as well, the numbers near the plotted point indicates the FDP/D dimer ratio. Among the 11 samples, 6 samples from A to F were determined as the enhanced fibrinolytic samples in the enhanced fibrinolytic state determination using the first determination and the second determination, and the 3 samples from I to J were determined as the non-enhanced fibrinolytic samples in the enhanced fibrinolytic state determination using the first determination and the second determination.

In the enhanced fibrinolytic state determination by the Western blotting, determination as enhanced fibrinolysis was made if a band was detected near 100 kDa. According to FIG. 21, the band was detected near 100 kDa excluding the sample of B in the 6 samples from A to F, and the band was not detected near 100 kDa in the 3 samples from I to K. Therefore, the enhanced fibrinolytic state determination using the first determination and the second determination have more or less the same results as the enhanced fibrinolytic state determination by the Western blotting, and satisfactory results were obtained.

4. FDP/D Dimer Ratio Estimation and D Dimer Concentration Estimation

4.1 Estimating Method

As described above, the processing device 30 can give a value related to the D dimer in addition to or in place of determining the enhanced fibrinolytic state in step S14 of FIG. 1. The values related to the D dimer obtained by the processing device 30 are an estimated value of the FDP/D dimer ratio and an estimated value of the D dimer concentration.

The processing device 30 obtains the estimated value of the FDP/D dimer ratio and the estimated value of the D dimer concentration based on the first information indicating the FDP concentration and the second information indicating the area of the convex area. The processing device 30 calculates the estimated value of the FDP/D dimer ratio using the following formula (4). Formula (4) is stored in the memory 32 as analysis information 32d.

[Formula 4]

$$\text{FDP}/D \text{ dimer ratio} = 10.77 e^{(-7.06x)} \quad (4)$$

x: area of convex area per FDP unit concentration

The area of the convex area per an FDP concentration of 1 μg/ml in formula (4) is calculated by area of convex area/FDP concentration. Therefore, the area of the convex area per an FDP concentration of 1 μg/ml can be calculated based on the first information indicating the FDP concentration and the second information indicating the area of the convex area.

The processing device 30 calculates the estimated value of the D dimer concentration based on the following formula (5) from the estimated value of the FDP/D dimer ratio. Formula (5) is stored in the memory 32 as analysis information 3e.

[Formula 5]

$$D \text{ dimer concentration} = \text{FDP concentration}/(\text{FDP}/D \text{ dimer ratio}) \quad (5)$$

4.2 Verification of Estimating Method

4.2.1 Calculation of Formula (4)

First, the calculation procedure of formula (4) will be described. The FDP measurement and the D dimer measurement were conducted using the FDP measurement specimen and the D dimer measurement specimen prepared from a plurality of blood plasma samples. The time course curve of the OD value was obtained from the respective measurement. The FDP concentration and the D dimer concentration were calculated from the time course curve obtained by the measurement of each of the attached documents. The FDP/D dimer ratio, which is the ratio between the FDP concentration and the D dimer concentration, was calculated from the FDP concentration and the D dimer concentration. The area of the convex area was calculated according to formula (1) from the time course curve obtained by the FDP measurement. The area of the convex area per an FDP concentration of 1 µg/ml was calculated from the area of the convex area and the FDP concentration.

Figure 23:
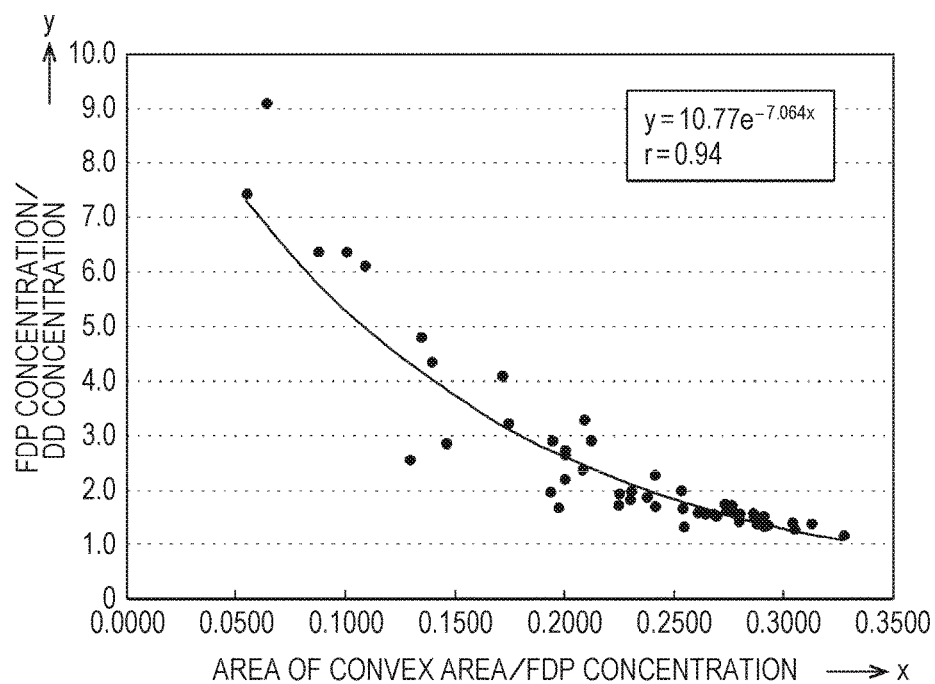
FIG. 23 is a graph showing a relationship between the area of the convex area/FDP concentration and the FDP/D dimer ratio.

The relationship between the calculated FDP/D dimer ratio and the area of the convex area per an FDP concentration of 1 µg/ml was approximated by an exponential function to obtain formula (4). In FIG. 23, an approximation curve expressed by formula (4) is drawn on a graph in which the calculated FDP/D dimer ratio and the area of the convex area per an FDP concentration of 1 µg/ml are plotted.

As is apparent from FIG. 23, a predetermined relationship is found between the FDP/D dimer ratio and the area of the convex area per an FDP concentration of 1 µg/ml, so that the estimated value of the FDP/D dimer ratio can be obtained using formula (4), for example, when the area of the convex area per an FDP concentration of 1 µg/ml is obtained.

4.2.2 Verification of Formula (4) and Formula (5)

Figure 24:
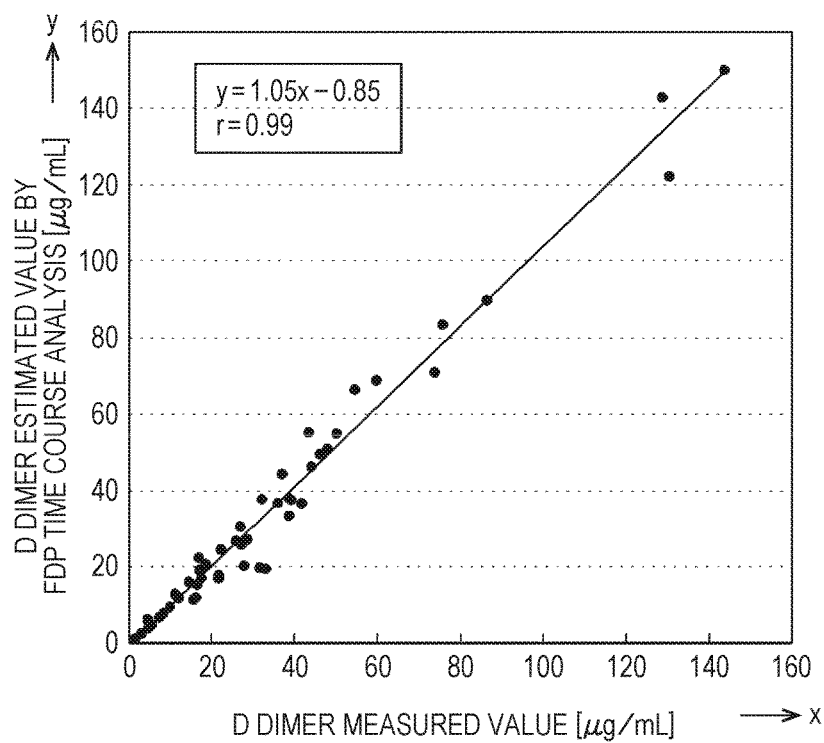
FIG. 24 is a graph showing a relationship between a D dimer measured value and a D dimer estimated value by the FDP time course analysis.

The area of the convex area per an FDP concentration of 1 µg/ml was obtained from the FDP concentration and the area of the convex area obtained from 54 samples in the second setting example described above, and the FDP/D dimer ratio was estimated based on formula (4). According to formula (5), the FDP concentration was divided by the estimated FDP/D dimer ratio based on formula (4) to calculate the estimated D dimer concentration. The results are shown in FIG. 24. The horizontal axis of FIG. 24 indicates a measured value of the D dimer of each sample. The measured value of the D dimer is the D dimer concentration obtained by measuring a specimen, which is prepared by mixing the sample with the D dimer measuring reagent. The vertical axis of FIG. 24 indicates a D dimer estimated value by the FDP time course analysis of each sample. The D dimer estimated value by the FDP time course analysis is the estimated value of the D dimer concentration obtained by formula (4) and formula (5).

As is apparent from FIG. 24, the measured value of the D dimer and the estimated value of the D dimer concentration show high correlation (correlation coefficient r=0.99), and hence the estimation of the D dimer concentration is satisfactory. As the estimation of the D dimer concentration is satisfactory, the estimation of the FDP/D dimer ratio is also confirmed to be satisfactory.

5. Sample Analysis Result Display

After the analyzing process up to step S14 of FIG. 1 is completed, the processing device 30 displays a result display screen 100 shown in FIG. 25 on the display 33. The result display screen 100 includes display regions of an enhanced fibrinolytic flag 101, an FDP/DD estimated value 102, and a DD estimated value 103, other than a measurement date and time, sample number, and FDP measured value indicating the FDP concentration for each sample. The enhanced fibrinolytic flag 101 indicates whether or not the sample is determined to be in the enhanced fibrinolytic state. For the sample determined to be in the enhanced fibrinolytic state, "enhanced fibrinolysis" is displayed in the region of the enhanced fibrinolytic flag 101.

The region of the FDP/DD estimated value 102 displays the estimated value of the FDP/D dimer ratio, and the region of the DD estimated value 103 displays the estimated value of the D dimer concentration.

Figure 26:
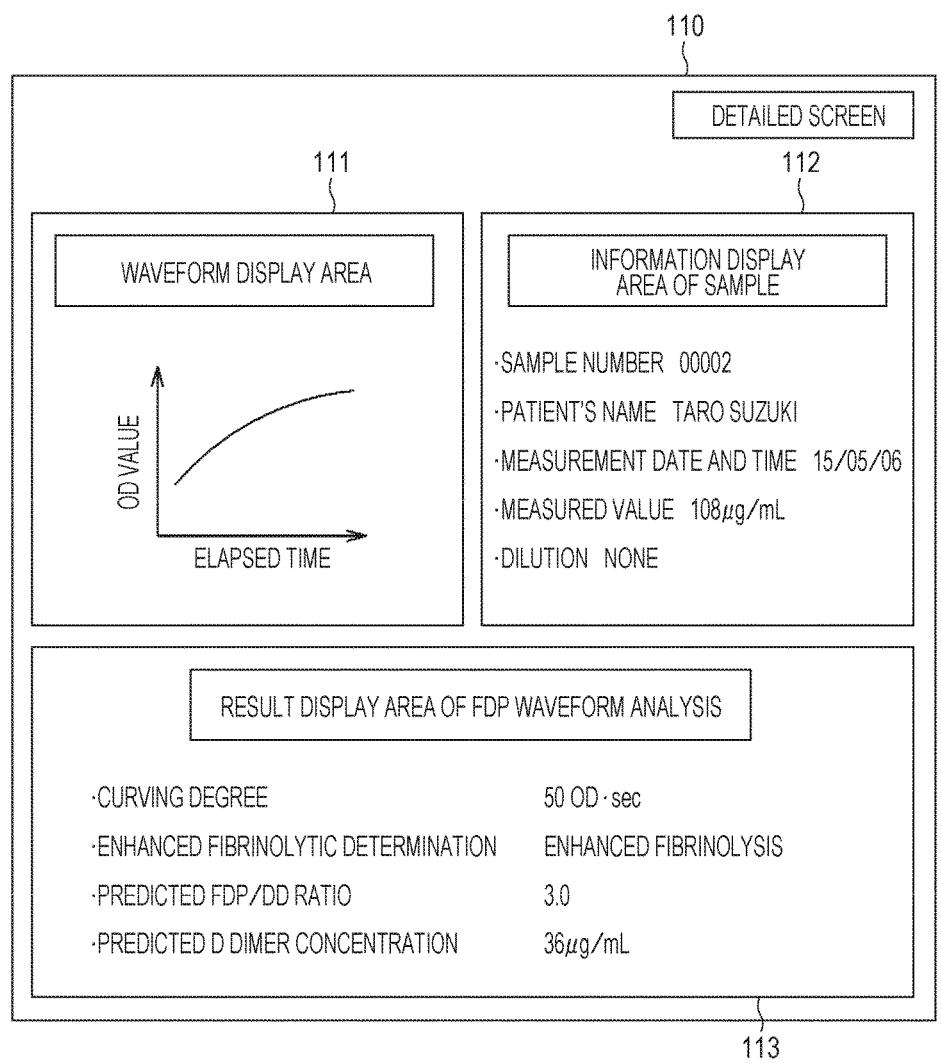
FIG. 26 is a diagram showing a detailed display screen.

When receiving the specification of a specific sample in the result display screen 100 from a user by click of the mouse, for example, the processing device 30 displays a detailed screen 110 displaying the detailed information related to the relevant sample. As shown in FIG. 26, the detailed screen 110 includes a waveform display area 111, an information display area 112 of a sample, and a result display area 113 of the FDP waveform analysis.

The waveform display area 111 is a region for displaying the time course curve obtained from the measurement specimen for the FDP measurement. The information display area 112 of the sample includes a display of, for example, sample number, patient's name, measurement date and time, measured value of FDP concentration, and dilution/non-dilution. The result display area 113 of the FDP waveform analysis includes the curving degree of the time course curve, enhanced fibrinolytic determination result, estimated value of the FDP/D dimer ratio, estimated value of the D dimer concentration, and the like. Thus, the diagnosis of the enhanced fibrinolysis by a doctor can be assisted by displaying information obtained by the sample analysis.

In the embodiment described above, the enhanced fibrinolytic state determination and the estimation of the D dimer concentration were carried out by the FDP measurement without carrying out the D dimer measurement, but the D dimer measurement may be further carried out. For example, after carrying out the enhanced fibrinolytic state determination by the FDP measurement without carrying out the D dimer measurement as a primary screening, the D dimer measurement may be carried out to obtain the FDP/D dimer ratio and carry out the enhanced fibrinolytic state determination as a secondary examination. If the value of the D dimer concentration obtained by the D dimer measurement is an abnormal value, whether the value of the D dimer concentration is really an abnormal value can be checked using the estimated value of the D dimer concentration obtained by the FDP measurement. Thus, the D dimer measurement may be carried out when implementing the present invention.

What is claimed is:

1. A blood sample analyzing method comprising:
preparing a measurement specimen by mixing a blood sample with a measuring reagent of degradation products of fibrin and fibrinogen (FDP);
acquiring, based on a time-dependent change in optical information obtained by optically measuring the measurement specimen, first information indicating an FDP concentration and second information indicating a curving degree of a time course curve showing the time-dependent change of the optical information; and
determining an enhanced fibrinolytic state of the blood sample or acquiring an estimated value of a D dimer concentration or a value calculated from a D dimer concentration of the blood sample based on the first information and the second information.

2. The blood sample analyzing method according to claim 1, wherein determining the enhanced fibrinolytic state of the blood sample includes comparing a value obtained by applying the FDP concentration indicated by the first information to an evaluation function proportional to the FDP concentration, with the second information.

3. The blood sample analyzing method according to claim 2, wherein determining the enhanced fibrinolytic state of the blood sample further includes comparing the FDP concentration indicated by the first information with a threshold value.

4. The blood sample analyzing method according to claim 1, wherein the second information indicates the curving degree of the time course curve by a size of a region surrounded by a line connecting a starting point with a terminating point set on the time course curve, and the time course curve.

5. The blood sample analyzing method according to claim 1, wherein the optical information is an optical concentration value.

6. The blood sample analyzing method according to claim 1, wherein the value calculated from the D dimer concentration includes an FDP/D dimer ratio.

7. The blood sample analyzing method according to claim 1, comprising acquiring the estimated value of a D dimer concentration.

8. A blood sample analyzer comprising:
a specimen preparing unit that prepares a measurement specimen by mixing a blood sample with a measuring reagent of degradation products of fibrin and fibrinogen (FDP);
a detection unit that optically measures the measurement specimen and outputs a detection signal; and
a processing unit that acquires, based on optical information of the measurement specimen obtained from the detection signal, first information indicating an FDP concentration and second information indicating a curving degree of a time course curve showing a time-dependent change of the optical information, and determines an enhanced fibrinolytic state of the blood sample or acquires an estimated value of a D dimer concentration or a value calculated from a D dimer concentration of the blood sample based on the first information and the second information.

9. The blood sample analyzer according to claim 8, further comprising:
a storage unit that stores an evaluation function proportional to the FDP concentration; wherein
the processing unit determines the enhanced fibrinolytic state of the blood sample by comparing a value obtained by applying the FDP concentration indicated by the first information to the evaluation function, with the second information.

10. The blood sample analyzer according to claim 9, wherein the processing unit determines the enhanced fibrinolytic state of the blood sample by comparing the FDP concentration indicated by the first information with a threshold value, and comparing a value obtained by applying the FDP concentration indicated by the first information to the evaluation function, with the second information.

11. The blood sample analyzer according to claim 8, wherein the second information indicates the curving degree of the time course curve by a size of a region surrounded by a line connecting a starting point with a terminating point set on the time course curve, and the time course curve.

12. The blood sample analyzer according to claim 8, wherein the optical information is an optical concentration value.

13. The blood sample analyzer according to claim 8, wherein the value calculated from the D dimer concentration includes an FDP/D dimer ratio.

14. The blood sample analyzer according to claim 8, wherein the processing unit acquires the estimated value of a D dimer concentration.

15. A system configured to perform a sample analyzing process, comprising:
a processor, and
a memory, under control of the processor, including software instructions for executing the sample analyzing process, wherein the processor is configured to execute the software instructions by performing:
a first process of acquiring, based on a time-dependent change of optical information obtained by optically measuring a measurement specimen that is a mixture of a measuring reagent of degradation products of fibrin and fibrinogen (FDP) and a blood sample, first information indicating an FDP concentration and second information indicating a curving degree of a time course curve showing the time-dependent change of the optical information; and
a second process of determining an enhanced fibrinolytic state of the blood sample based on the first information and the second information.

16. The system according to claim 15, wherein the processor is further configured to:
store an evaluation function proportional to the FDP concentration; wherein
the second process of determining comprises determining the enhanced fibrinolytic state of the blood sample by comparing a value obtained by applying the FDP concentration indicated by the first information to the evaluation function, with the second information.

17. The system according to claim 16, wherein second process of determining comprises determining the enhanced fibrinolytic state of the blood sample by comparing the FDP concentration indicated by the first information with a threshold value, and comparing a value obtained by applying the FDP concentration indicated by the first information to the evaluation function, with the second information.

18. The system according to claim 15, wherein the second information indicates the curving degree of the time course curve by a size of a region surrounded by a line connecting a starting point with a terminating point set on the time course curve, and the time course curve.

19. The system according to claim 15, wherein the optical information is an optical concentration value.

20. The system according to claim 15, wherein the processor is further configured to acquire an FDP/D dimer ratio or a D dimer concentration of the blood sample based on the first information and the second information.

* * * * *